United States Patent
Yamaji et al.

(10) Patent No.: US 8,283,291 B2
(45) Date of Patent: Oct. 9, 2012

(54) HERBICIDAL COMPOSITION

(75) Inventors: Yoshihiro Yamaji, Taitoh-ku (JP);
Hisashi Honda, Taitoh-ku (JP);
Masanori Kobayashi, Taitoh-ku (JP);
Ryo Hanai, Taitoh-ku (JP)

(73) Assignee: Kumiai Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/293,842

(22) Filed: Nov. 10, 2011

(65) Prior Publication Data

US 2012/0058896 A1 Mar. 8, 2012

Related U.S. Application Data

(63) Continuation of application No. 11/948,542, filed on Nov. 30, 2007, now Pat. No. 8,110,530.

(60) Provisional application No. 60/885,696, filed on Jan. 19, 2007.

(30) Foreign Application Priority Data

Dec. 21, 2006 (JP) ................................ 2006-344409

(51) Int. Cl.
*A01N 43/02* (2006.01)
*A01N 43/10* (2006.01)
(52) U.S. Cl. ..................................... 504/156; 504/116.1
(58) Field of Classification Search ............... 504/116.1, 504/156
See application file for complete search history.

(56) References Cited

U.S. PATENT DOCUMENTS

| 6,534,444 | B1 | 3/2003 | Sievernich et al. |
| 6,872,691 | B2 * | 3/2005 | Schmitt et al. ................. 504/282 |
| 7,238,689 | B2 | 7/2007 | Nakatani et al. |
| 7,833,939 | B2 * | 11/2010 | Takahashi et al. ............ 504/156 |
| 2005/0256004 | A1 | 11/2005 | Takahashi et al. |
| 2009/0042727 | A1 | 2/2009 | Evans |

FOREIGN PATENT DOCUMENTS

| WO | 02/062770 A1 | 8/2002 |
| WO | 2004/014138 A1 | 2/2004 |
| WO | 2005/104848 A1 | 11/2005 |
| WO | 2006024820 A1 | 3/2006 |
| WO | 2006/097509 A2 | 9/2006 |
| WO | 2006/097509 A3 | 9/2006 |
| WO | 2007/006409 A2 | 1/2007 |

OTHER PUBLICATIONS

Analogue. (2011). In thefreedictionary.com. Retrieved Dec. 7, 2011, from http://www.merriam-webster.com/dictionary/analogue.*
Wermuth (Drug Discovery Today, 2006, 11(7/8), 348-354).*
"The Pesticide Manual", A World Compendium, 14$^{th}$ Edition, British Crop Council, 2006, 69 pages.
Shibuya Index (Index of Pesticides), 12$^{th}$ Edition, Shibuya Index Research Group, 2007, 83 pages.
Monthly Fine Chemical, vol. 35, No. 7, 2006, 12 pages.
New Zealand Office Action dated Sep. 9, 2010 in corresponding New Zealand Application No. 576518.

* cited by examiner

*Primary Examiner* — Fereydoun G Sajjadi
*Assistant Examiner* — Courtney Brown
(74) *Attorney, Agent, or Firm* — Oblon, Spivak, McClelland, Maier & Neustadt, L.L.P.

(57) ABSTRACT

The present invention relates to a herbicidal composition having a synergistic herbicidal effect against weeds, said herbicidal composition including 3-[(5-difluoromethoxy-1-methyl-3-trifluoromethylpyrazol-4-yl)methylsulfonyl]-4,5-dihydro-5,5-dimethylisoxazole and salts thereof as a component A and a component B selected from the group consisting of paraquat, ametryn, acetochlor, clodinafop-propargyl, diclofop-methyl, cycloxydim, tepraloxydim, tralkoxydim, amidosulfuron, mesosulfuron-methyl, sulfosulfuron, tribenuron-methyl, imazamethabenz-methyl, imazamox, imazapic, florasulam, hexazinone, chlorotoluron, pyraflufen-ethyl, metazachlor, S-metolachlor, isoxaben, fluroxypyr, qinclorac and pinoxaden.

13 Claims, No Drawings

HERBICIDAL COMPOSITION

CROSS-REFERENCE TO RELATED APPLICATIONS

This application is a divisional of U.S. patent application Ser. No. 11/948,542 filed Nov. 30, 2007, claims priority from U.S. provisional application No. 60/885,696 filed Jan. 19, 2007 and claims foreign priority from Japanese patent application no. 2006-344409 filed Dec. 21, 2006.

TECHNICAL FIELD

The present invention relates to a novel herbicidal composition.

BACKGROUND ART

It is disclosed in Patent Document 1 that isoxazoline derivatives or their salts as compounds of Component A to be incorporated in the herbicidal composition of the present invention are safe to rice, wheat, barley, corn, grain sorghum, soybean, cotton, sugar beet, lawn grass, fruits and the like and have excellent herbicidal effects by themselves.

Further, compounds of the after-mentioned Components B and C to be incorporated in the herbicidal composition of the present invention, are known compounds having herbicidal activities, and they are disclosed, for example, in Non-patent Documents 1 to 3.

Further, a group of compounds of the after-mentioned Component D to be incorporated in the herbicidal composition of the present invention, as the case requires, are compounds known as phytotoxicity-reducing agents, and such compounds are disclosed in Non-patent Documents 1 and 2.

Patent Document 2 discloses Examples wherein compounds represented by the formula [I] can be mixed with known herbicidal compounds.

On the other hand, various herbicides have been developed for practical use by the research and development over many years, and such herbicides have contributed to saving of weed-controlling operations or to the improvement of productivity of agricultural or horticultural crop plants. However, even today, it is desired to develop a novel herbicide which is safer and has excellent herbicidal characteristics.

Further, a herbicide to be used for crop plants is desired to be an agent which exhibits sufficient herbicidal effects against a wide range of weeds at a low dose by application to soil or foliage and yet exhibits high selectivity between crop plants and weeds.
Patent Document 1: WO2002/062770
Patent Document 2: WO2004/014138
Non-patent Document 1: Pesticide Manual 14th edition, British Crop Council
Non-patent Document 2: SHIBUYA INDEX 12th Edition, published by SHIBUYA INDEX RESEARCH ASSOCIATION
Non-patent Document 3: Monthly Fine Chemical, vol 35, No. 7 (2006), published by CMC

DISCLOSURE OF THE INVENTION

Object to be Accomplished by the Invention

It is an object of the present invention to provide a herbicidal composition comprising an isoxazoline derivative represented by the following formula [I] or its salt in order to control unwanted weeds in cultivation of crop plants or useful plants.

Means to Accomplish the Object

The present inventors have conducted an extensive research to accomplish the above object and as a result, have found that by the combined use of Component A which is a compound selected from isoxazoline derivatives represented by the following formula [I] and their salts, and a herbicide shown by the following Component B; by the combined use of Components A and B and a herbicide shown by the following Component C; by the combined use of Components A and B and a phytotoxicity-reducing agent shown by the following Component D; or by the combined use of Components A, B, C and D, not only the respective herbicidal effects are obtainable merely additively, but also synergistic herbicidal effects can be obtained, or the phytotoxicity can be synergistically reduced.

Namely, the present inventors have found that by the combined use of two or more such agents, the herbicidal spectrum can be broadened as compared with the herbicidal ranges of the respective agents, and at the same time, the herbicidal effects can be attained at an early stage; the effects are prolonged; further, sufficient effects are obtainable at a dose lower than the dose when they are used individually; at the same time, safety to rice, wheat, barley, corn, grain sorghum, soybean, cotton, sugar beet, lawn grass, fruits or the like is secured; and sufficient herbicidal effects can be obtained by single application. The present invention has been accomplished on the basis of such discoveries.

The present invention provides the following.
1. A herbicidal composition comprising the following Component A which is at least one compound selected from the group consisting of isoxazoline derivatives of the formula [I] and their salts, and the following Component B, as active ingredients:
Component A:

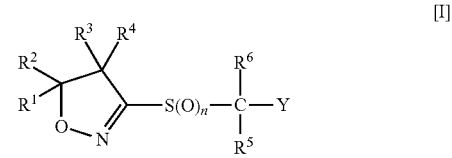

wherein each of $R^1$ and $R^2$ which are independent of each other, is a hydrogen atom, a $C_1$-$C_{10}$ alkyl group, a $C_3$-$C_8$ cycloalkyl group or a $C_3$-$C_8$ cycloalkyl $C_1$-$C_3$ alkyl group, or $R^1$ and $R^2$ together form a $C_3$-$C_7$ spiro ring together with the carbon atom to which they are bonded;
each of $R^3$ and $R^4$ which are independent of each other, is a hydrogen atom, a $C_1$-$C_{10}$ alkyl group, a $C_3$-$C_8$ cycloalkyl group, or $R^3$ and $R^4$ together form a $C_3$-$C_7$ spiro ring together with the carbon atom to which they are bonded, or $R^1$, $R^2$, $R^3$ and $R^4$ may form a 5- to 8-membered ring together with the carbon atoms to which they are bonded;
each of $R^5$ and $R^6$ which are independent of each other, is a hydrogen atom or a $C_1$-$C_{10}$ alkyl group;
Y is a 5- or 6-membered aromatic heterocyclic or aromatic condensed heterocyclic group having an optional hetero atom selected from the group consisting of a nitrogen atom, an oxygen atom and a sulfur atom, such a heterocyclic group may be substituted by from 0 to 6 same or different groups selected from the following substituent group α, adjacent two alkyl groups, alkoxy groups, alkyl and alkoxy groups, alkyl and alkylthio groups, alkyl and alkylsulfonyl groups, alkyl and monoalkylamino groups, or alkyl and dialkylamino groups may be bonded to each other to form a 5- to 8-membered ring which may be substituted by from 1 to 4 halogen atoms, and when the hetero atom of such a heterocyclic group is a nitrogen atom, it may be oxidized to be an N-oxide;

n is an integer of from 0 to 2;

Substituent Group α:

a hydroxyl group, a thiol group, a halogen atom, a $C_1$-$C_{10}$ alkyl group, a $C_1$-$C_{10}$ alkyl group mono-substituted by an optional group selected from the following substituent group β, a $C_1$-$C_4$ haloalkyl group, a $C_3$-$C_8$ cycloalkyl group, a $C_1$-$C_{10}$ alkoxy group, a $C_1$-$C_{10}$ alkoxy group mono-substituted by an optional group selected from the following substituent group γ, a $C_1$-$C_4$ haloalkoxy group, a $C_3$-$C_8$ cycloalkyloxy group, a $C_3$-$C_8$ cycloalkyl $C_1$-$C_3$ alkyloxy group, a $C_1$-$C_{10}$ alkylthio group, a $C_1$-$C_{10}$ alkylthio group mono-substituted by an optional group selected from the following substituent group γ, a $C_1$-$C_4$ haloalkylthio group, a $C_2$-$C_8$ alkenyl group, a $C_2$-$C_6$ alkenyloxy group, a $C_2$-$C_8$ alkynyl group, a $C_2$-$C_6$ alkynyloxy group, a $C_1$-$C_{10}$ alkylsulfinyl group, a $C_1$-$C_{10}$ alkylsulfinyl group mono-substituted by an optional group selected from the following substituent group γ, a $C_1$-$C_{10}$ alkylsulfonyl group, a $C_1$-$C_{10}$ alkylsulfonyl group mono-substituted by an optional group selected from the following substituent group γ, a $C_1$-$C_4$ haloalkylsulfinyl group, a $C_1$-$C_{10}$ alkylsulfonyloxy group mono-substituted by an optional group selected from the following substituent group γ, a $C_1$-$C_4$ haloalkylsulfonyl group, a $C_1$-$C_{10}$ alkylsulfonyloxy group, a $C_1$-$C_4$ haloalkylsulfonyloxy group, a phenyl group which may be substituted, a phenoxy group which may be substituted, a phenylthio group which may be substituted, an aromatic heterocyclic group which may be substituted, an aromatic heterocyclic oxy group which may be substituted, an aromatic heterocyclic thio group which may be substituted, a phenylsulfinyl group which may be substituted, a phenylsulfonyl group which may be substituted, an aromatic heterocyclic sulfonyl group which may be substituted, a phenylsulfonyloxy group which may be substituted, an acyl group, a $C_1$-$C_4$ haloalkylcarbonyl group, a benzylcarbonyl group which may be substituted, a benzoyl group which may be substituted, a carboxyl group, a $C_1$-$C_{10}$ alkoxycarbonyl group, a benzyloxycarbonyl group which may be substituted, a phenoxycarbonyl group which may be substituted, a cyano group, a carbamoyl group (a nitrogen atom of this group may independently be substituted by a $C_1$-$C_{10}$ alkyl group or a phenyl group which may be substituted), a $C_1$-$C_6$ acyloxy group, a $C_1$-$C_4$ haloalkylcarbonyloxy group, a benzylcarbonyloxy group which may be substituted, a benzoyloxy group which may be substituted, a nitro group, and an amino group (a nitrogen atom of this group may independently be substituted by a $C_1$-$C_{10}$ alkyl group, a phenyl group which may be substituted, a $C_1$-$C_6$ acyl group, a $C_1$-$C_4$ haloalkylcarbonyl group, a benzylcarbonyl group which may be substituted, a benzoyl group which may be substituted, a $C_1$-$C_{10}$ alkylsulfonyl group, a $C_1$-$C_4$ haloalkylsulfonyl group, a benzylsulfonyl group which may be substituted, or a phenylsulfonyl group which may be substituted);

Substituent Group β:

a hydroxyl group, a $C_3$-$C_8$ cycloalkyl group (this group may be substituted by a halogen atom or an alkyl group), a $C_1$-$C_{10}$ alkoxy group, a $C_1$-$C_{10}$ alkylthio group, a $C_1$-$C_{10}$ alkylksulfonyl group, a $C_1$-$C_{10}$ alkoxycarbonyl group, a $C_2$-$C_6$ haloalkenyl group, an amino group (a nitrogen atom of this group may independently be substituted by a $C_1$-$C_{10}$ alkyl group, a $C_1$-$C_6$ acyl group, a $C_1$-$C_4$ haloalkylcarbonyl group, a $C_1$-$C_{10}$ alkylsulfonyl group, or a $C_1$-$C_4$ haloalkylsulfonyl group), a carbamoyl group (a nitrogen atom of this group may independently be substituted by a $C_1$-$C_{10}$ alkyl group), a $C_1$-$C_6$ acyl group, a $C_1$-$C_4$ haloalkylcarbonyl group, a $C_1$-$C_{10}$ alkoxyimino group, a cyano group, a phenyl group which may be substituted, and a phenoxy group which may be substituted;

Substituent Group γ:

a $C_1$-$C_{10}$ alkoxycarbonyl group, a phenyl group which may be substituted, an aromatic heterocyclic group which may be substituted, a cyano group, and a carbamoyl group (a nitrogen atom of this group may independently be substituted by a $C_1$-$C_{10}$ alkyl group);

Component B:

At least one compound selected from the group consisting of:

(B-1) Acetyl CoA Carboxylase Inhibitors (a) Aryloxyphenoxypropionic Acid Compounds:

Clodinafop-propargyl, cyhalofop-butyl, diclofop-methyl, fenoxaprop-P-ethyl, fenoxaprop-ethyl, fluazifop-butyl, fluazifop-P-butyl, haloxyfop, haloxyfop-P, haloxyfop-P-methyl, metamifop, propaquizafop, quizalofop-ethyl, quizalofop-P, quizalofop-P-ethyl, quizalofop-P-tefuryl.

(b) Cyclohexanedione Compounds:

Alloxydim, butroxydim, clethodim, cycloxydim, profoxydim, sethoxydim, tepraloxydim, tralkoxydim.

(c) Phenylpyrazoline Compounds:

Aminopyralid.

(B-2) Branched Chain Amino Acid Synthesis Inhibitors (a) Sulfonylurea Compounds:

Amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, foramsulfuron, imazosulfuron, iodosulfulon-methyl-sodium, mesosulfuron-methyl, metsulfuron-methyl, oxasulfuron, pyrazosulfuron-ethyl, sulfometuron-methyl, sulfosulfuron, triasulfuron, tribenuron-methyl, trifloxysulfuron-sodium, triflusulfuron-methyl, tritosulfuron.

(b) Imidazolinone Compounds:

Imazamethabenz-methyl, imazamox, imazapic, Imazaquin.

(c) Triazolopyrimidine Compounds:

Diclosulam, florasulam, metosulam, penoxsulam.

(d) Pyrimidinyloxy(thio)benzoic Acid Compounds:

Bispyribac-sodium, pyribenzoxim, pyriftalid, pyriminobac-methyl, pyrithiobac-sodium.

(e) Sulfonylaminocarbonyltriazolinone Compound:

Flucarbazone-sodium.

(B-3) Photosynthesis II Inhibitors (a) Triazine Compounds:

Ametryn, dimethametryn, desmetryne, prometryn, propazine, simetryn, terbumeton, terbuthylazine, terbutryn, trietazine.

(b) Triazinone Compounds:

Hexazinone, metamitron.

(c) Triazolinone Compounds:

Amicarbazone.

(d) Uracil Compounds:

Bromacil, lenacil, terbacil.

(e) Pyridazinone Compounds:

Chloridazon.

(f) Phenylcarbamate Compounds:

Desmedipham, phenmedipham.

(g) Urea Compounds:
  Chlorbromuron, chlorotoluron, chloroxuron, dimefuron, diuron, ethidimuron, fenuron, fluometuron, isoproturon, isouron, methabenzthiazuron, metobromuron, metoxuron, monolinuron, neburon, siduron, tebuthiuron.
(h) Anilide Compounds:
  Pentanochlor, propanil.
(i) Hydroxybenzonitrile Compounds:
  Ioxynil, bromofenoxim.
(j) Benzothiadiazinone Compounds:
  Bentazone.
(k) Phenylpyridazine Compounds:
  Pyridate, pyridafol.
(B-4) Photosynthesis I Inhibitors
(a) Bipyridinium Compounds:
  Diquat, paraquat.
(B-5) Protoporphrin Synthesis Inhibitors
(a) Diphenyl Ether Compounds:
  Acifluorfen, bifenox, chlomethoxyfen, fluoroglycofen-ethyl, fomesafen, lactofen, oxyfluorfen.
(b) Phenylphthalimide Compounds:
  Cinidon-ethyl, flumiclorac-pentyl.
(c) Thiadiazole Compounds:
  Fluthiacet-methyl, thidiazimin.
(d) Oxadiazole Compounds:
  Oxadiargyl, oxadiazon.
(e) Triazolinone Compounds:
  Azafenidin, sulfentrazone.
(f) Pyrimidinedione Compounds:
  Butafenacil, benzfendizone.
(g) Oxazolidinedione Compounds:
  Pentoxazone.
(h) Phenylpyrazole Compounds:
  Pyraflufen-ethyl, fluazolate.
(i) Other Compounds:
  Pyraclonil, profluazol, flufenpyr-ethyl.
(B-6) 4-Hydroxyphenylpyruvate Dioxygenase Inhibitors, Carotenoid Synthesis Inhibitors
(a) Pyridazinone Compounds:
  Norflurazon.
(b) Triketone Compounds:
  Sulcotrione.
(c) Isoxazole Compounds:
  Isoxachlortole.
(d) Pyrazole Compounds:
  Benzofenap, pyrazolynate, pyrazoxyfen.
(e) Triazole Compounds:
  Amitrole.
(f) Isoxazolidinone Compounds:
  Clomazone.
(g) Pyridine Carboxamide Compounds:
  Picolinafen.
(h) Diphenyl Ether Compounds:
  Aclonifen.
(i) Urea Compounds:
  Fluometuron.
(j) Other Compounds:
  Beflubutamid, fluridone, flurochloridone, flurtamone, benzobicyclon.
(B-7) 5-Enolpyruvylshikimate-5-phosphate Synthesis Inhibitors
(a) Glycine Compounds:
  Sulfosate.
(B-8) Glutamine Synthesis Inhibitors
(a) Phosphinic Acid Compounds:
  Bilanafos.
(B-9) Folic Acid Synthesis Inhibitors
(a) Carbamate Compounds:
  Asulam.
(B-10) Cell Division Inhibitors, Ultralong Chain Fatty Acid Synthesis Inhibitors
(a) Dinitroaniline Compounds:
  Benfluralin, butralin, dinitramine, ethalfluralin, oryzalin, trifluralin.
(b) Pyridine Compounds:
  Dithiopyr, thiazopyr.
(c) Benzenedicarboxylic Acid Compounds:
  Chlorthal-dimethyl.
(d) Phosphoroamidate Compounds:
  Butamifos, amiprophos-methyl.
(e) Benzamide Compounds:
  Propyzamide, tebutam.
(f) Carbamate Compounds:
  Carbetamide, chlorpropham, propham.
(g) Chloroacetamide Compounds:
  Acetochlor, alachlor, butachlor, dimethachlor, dimethenamid, metazachlor, pethoxamid, pretilachlor, propachlor, propisochlor, S-metolachlor, thenylchlor.
(h) Oxyacetamide Compounds:
  Flufenacet, mefenacet.
(i) Tetrazolinone Compounds:
  Fentrazamide.
(j) Alkaneamide Compounds:
  Diphenamid, naproanilide, napropamide.
(i) Other compounds:
  Anilofos, cafenstrole, piperophos.
(B-11) Cellulose Synthesis Inhibitors
(a) Benzonitrile Compounds:
  Dichlobenil, chlorthiamid.
(b) Benzamide Compounds:
  Isoxaben.
(c) Triazolocarboxyamide Compounds:
  Flupoxame.
(B-12) Membrane Disruption Agents
(a) Dinitrophenol Compounds:
  Dinoterb, DNOC, dinoterb.
(B-13) Fatty Acid Synthesis Inhibitors
(a) Thiocarbamate Compounds:
  Butylate, cycloate, dimepiperate, EPTC, esprocarb, molinate, orbencarb, pebulate, prosulfocarb, thiobencarb, tiocarbazil, triallate, vernolate.
(b) Benzofuran Compounds:
  Benfuresate, ethofumesate.
(c) Chlorocarboxylic Acid Compounds:
  TCA, dalapon, flupropanate.
(d) Phosphorodithioate Compounds:
  Bensulide.
(B-14) Auxin Synthesis inhibitors
(a) Phenoxycarboxylic Acid Compounds:
  Clomeprop, 2,4-D, 2,4-DB, dichlorprop, dichlorprop-P, MCPA, MCPB, mecoprop, mecoprop-P, MCPA-thioethyl.
(b) Benzoic Acid Compounds:
  2,3,6-TBA, chloramben.
(c) Pyridine Carboxylic Acid Compounds:
  Fluroxypyr, picloram, triclopyr.
(d) Quinoline Carboxylic Acid Compounds:
  Quinclorac.
(e) Benzothiazole Compounds:
  Benazolin.
(B-15) Auxin Transport Inhibitors
(a) Semicarbazone Compounds:
  Diflufenzopyr.

(b) Phthalamate Compounds:
Naptalam.

(B-16) Other Inhibitors

Difenzoquat, flamprop-M, bromobutide, oxaziclomefone, cinmethylin, etobenzanid, fosamine, cumyluron, daimuron, methyl-dimuron, indanofan, pyributicarb, pyrimisulfan, HC-252, forchlorfenuron, thidiazuron, pyrasulfotole, maleic hydrazide, diflumetorim, fenclorim, ancymidol, flurprimidol, chlormequat, mepiquatchloride, quinmerac, propoxycarbazone-sodium, propoxycarbazone, flucetosulfuron, tefuryltrion, karbutilate, metobenzuron, prodiamine, pyroxsulam, triaziflam, pinoxaden, bencarbazone, trinexapac-ethyl and prohexadione-calcium, and their salts and analogues such as acids, esters and amides.

2. The herbicidal composition according to the above 1, wherein Component A is a compound of the formula [I] wherein Y is a 5- or 6-membered aromatic heterocyclic group having a hetero atom selected from the group consisting of a nitrogen atom, an oxygen atom and a sulfur atom.

3. The herbicidal composition according to the above 1, wherein Component A is a compound of the formula [I] wherein Y is a thienyl group, a pyrazolyl group, an isoxazolyl group, an isothiazolyl group, a pyridyl group or a pyrimidinyl group.

4. The herbicidal composition according to the above 1, wherein Component A is a compound of the formula [I] wherein Y is a thiophen-3-yl group, a pyrazol-4-yl group, a pyrazol-5-yl group, an isoxazol-4-yl group, an isothiazol-4-yl group, a pyridin-3-yl group or a pyrimidin-5-yl group.

5. The herbicidal composition according to the above 1, wherein Component A is a compound of the formula [I] wherein Y is a pyrazol-4-yl group wherein the pyrazole ring is substituted at the 3- and 5-positions by the substituent group a and at the 1-position by a hydroxyl group, a $C_1$-$C_{10}$ alkyl group, a $C_1$-$C_{10}$ alkyl group mono-substituted by an optional group selected from the substituent group β, a $C_1$-$C_4$ haloalkyl group, a $C_3$-$C_8$ cycloalkyl group, a $C_2$-$C_6$ alkenyl group, a $C_2$-$C_6$ alkynyl group, a $C_1$-$C_{10}$ alkylsulfinyl group, a $C_1$-$C_{10}$ alkylsulfonyl group, a $C_1$-$C_{10}$ alkylsulfonyloxy group mono-substituted by an optional group selected from the substituent group γ, a $C_1$-$C_4$ haloalkylsulfonyl group, a phenyl group which may be substituted, an aromatic heterocyclic group which may be substituted, a phenylsulfonyl group which may be substituted, an aromatic heterocyclic sulfonyl group which may be substituted, an acyl group, a $C_1$-$C_4$ haloalkylcarbonyl group, a benzylcarbonyl group which may be substituted, a benzoyl group which may be substituted, a carboxyl group, a $C_1$-$C_{10}$ alkoxycarbonyl group, a benzyloxycarbonyl group which may be substituted, a phenoxycarbonyl group which may be substituted, a carbamoyl group (a nitrogen atom of this group may independently be substituted by a $C_1$-$C_{10}$ alkyl group or a phenyl group which may be substituted), or an amino group (a nitrogen atom of this group may independently be substituted by a $C_1$-$C_{10}$ alkyl group, a phenyl group which may be substituted, an acyl group, a $C_1$-$C_4$ haloalkylcarbonyl group, a benzylcarbonyl group which may be substituted, a benzoyl group which may be substituted, a $C_1$-$C_{10}$ alkylsulfonyl group, a $C_1$-$C_4$ haloalkylsulfonyl group, a benzylsulfonyl group which may be substituted, or a phenylsulfonyl group which may be substituted).

6. The herbicidal composition according to the above 1, wherein Component A is a compound of the formula [I] wherein Y is a pyrazol-5-yl group wherein the pyrazole ring is substituted at the 4-position by the substituent group α and at the 1-position by a hydroxyl group, a $C_1$-$C_{10}$ alkyl group, a $C_1$-$C_{10}$ alkyl group mono-substituted by an optional group selected from the substituent group β, a $C_1$-$C_4$ haloalkyl group, a $C_3$-$C_8$ cycloalkyl group, a $C_2$-$C_6$ alkenyl group, a $C_2$-$C_6$ alkynyl group, a $C_1$-$C_{10}$ alkylsulfinyl group, a $C_1$-$C_{10}$ alkylsulfonyl group, a $C_1$-$C_{10}$ alkylsulfonyl group mono-substituted by an optional group selected from the substituent group γ, a $C_1$-$C_4$ haloalkylsulfonyl group, a phenyl group which may be substituted, an aromatic heterocyclic group which may be substituted, a phenylsulfonyl group which may be substituted, an aromatic heterocyclic sulfonyl group which may be substituted, an acyl group, a $C_1$-$C_4$ haloalkylcarbonyl group, a benzylcarbonyl group which may be substituted, a benzoyl group which may be substituted, a carboxyl group, a $C_1$-$C_{10}$ alkoxycarbonyl group, a benzyloxycarbonyl group which may be substituted, a phenoxycarbonyl group which may be substituted, a carbamoyl group (a nitrogen atom of this group may independently be substituted by a $C_1$-$C_{10}$ alkyl group or a phenyl group which may be substituted), or an amino group (a nitrogen atom of this group may independently be substituted by a $C_1$-$C_{10}$ alkyl group, a phenyl group which may be substituted, an acyl group, a $C_1$-$C_4$ haloalkylcarbonyl group, a benzylcarbonyl group which may be substituted, a benzoyl group which may be substituted, a $C_1$-$C_{10}$ alkylsulfonyl group, a $C_1$-$C_4$ haloalkylsulfonyl group, a benzylsulfonyl group which may be substituted, or a phenylsulfonyl group which may be substituted).

7. The herbicidal composition according to the above 1, wherein Component A is a compound of the formula [I] wherein each of $R^1$ and $R^2$ is a methyl group, each of $R^3$ and $R^4$ is a hydrogen atom, and Y is a pyrazol-4-yl group wherein the pyrazole ring is substituted at the 1-, 3- and 5-positions independently by a $C_1$-$C_4$ alkyl group, a $C_1$-$C_4$ haloalkyl group or a $C_1$-$C_4$ haloalkoxy group.

8. The herbicidal composition according to the above 1, wherein Component A is 3-[(5-difluoromethoxy-1-methyl-3-trifluoromethylpyrazol-4-yl)methylsulfonyl]-4,5-dihydro-5,5-dimethylisoxazole.

9. The herbicidal composition according to any one of the above 1 to 8, wherein Component B is at least one compound selected from the group consisting of quizafop-ethyl, quizafop-P-ethyl, sethoxydim, pyrithiobac-sodium, bispyribac-sodium, pyrimisulfan, imazethapyr, imazaquin, chlorimuron-ethyl, diuron, bentazone, paraquat, sulfentrazone, fluthiacet-methyl, sulcotrione, norflurazon, clomazone, bilanafos, asulam, flufenacet, dimethenamid-P, prosulfocarb, thiobencarb, 2,4-D, clopyralid, ametryn, isoproturon, picolinafen, trifluralin, acetochlor and triallate.

10. The herbicidal composition according to any one of the above 1 to 8, wherein Component B is imazaquin, diuron, sulfentrazone, sulcotrione, norflurazon, clomazone, dimethenamid-P, prosulfocarb, isoproturon, trifluralin or triallate.

11. A herbicidal composition comprising the herbicidal composition as defined in any one of the above 1 to 10 and the following Component C, as active ingredients:

Component C:

At least one compound selected from the group consisting of atrazine, simazine, cyanazine, isoxaflutole, mesotrione, flumetsulam, imazethapyr, imazapyr, dicamba, clopyralid, prosulfuron, halosulfuron-methyl, rimsulfuron, bentazon, carfentrazone-ethyl, metribuzin, thifensulfuron-methyl, nicosulfuron, primisulfuron-methyl, cloransulam-methyl, glufosinate, glyphosate, sulfosate, pendimethalin, linuron, prometryne, diflufenican, flumioxazin, metolachlor, their salts and analogues.

12. A herbicidal composition comprising the herbicidal composition as defined in any one of the above 1 to 10 and the following Component D, as active ingredients:

Component D:

At least one compound selected from the group consisting of Cloquintocet-Mexyl, fenchlorazole, fenchlorazole-ethyl, mefenpyr, mefenpyr-diethyl, isoxadifen, isoxadifen-ethyl, furilazole, benoxacor, dichlormid, MON4660, oxabetrinil, cyometrinil, fenclorim, cyprosulfamide, naphthalic anhydride, Flurazole, their salts and analogues.

13. A herbicidal composition comprising the herbicidal composition as defined in the above 11 and Component D as defined in Claim 12, as active ingredients.

14. The herbicidal composition according to any one of the above 1 to 10, wherein the weight ratio of Component A:Component B is from 1:0.001 to 1:100.

15. The herbicidal composition according to the above 11, wherein the weight ratio of Component A:Component B:Component C is from 1:0.001:0.001 to 1:100:100.

16. The herbicidal composition according to the above 12, wherein the weight ratio of Component A:Component B:Component D is from 1:0.001:0.001 to 1:100:100.

17. The herbicidal composition according to the above 13, wherein the weight ratio of Component A:Component B:Component C:Component D is from 1:0.001:0.001:0.001 to 1:100:100:100.

18. A herbicidal composition comprising the herbicidal composition as defined in any one of the above 1 to 17 in an amount to show a herbicidal activity and at least one inert liquid carrier and/or solid carrier and, if necessary, further containing at least one surfactant.

19. A method for preparing the herbicidal composition as defined in any one of the above 1 to 18, which comprises mixing Component A and Component B; if necessary, Component C and/or Component D; at least one inert liquid carrier and/or solid carrier; and a surfactant.

20. A method for controlling unwanted plants, which comprises applying the active ingredients contained in the herbicidal composition as defined in any one of the above 1 to 18, simultaneously or dividedly, before, during and/or after germination of the unwanted plants.

Effects of the Invention

The herbicidal composition of the present invention is not limited to a simple sum of activities obtainable by the individual components and provides herbicidal effects or phytotoxicity-reducing effects synergistically, whereby the dose of the agricultural chemicals can be reduced. Further, it is highly safe to crop plants and capable of controlling various weeds problematic in e.g. paddy fields, upland fields, non-agricultural fields, etc., over a wide range of from pre-emergence to post-emergence.

BEST MODE FOR CARRYING OUT THE INVENTION

Now, definitions of terms used in this specification will be shown below.

An expression like "$C_1$-$C_{10}$" means that in this case, the carbon number of a substituent following the expression is from 1 to 10.

The halogen atom represents a fluorine atom, a chlorine atom, a bromine atom or an iodine atom.

The $C_1$-$C_{10}$ alkyl group represents a straight chain or branched chain alkyl group having a carbon number of from 1 to 10, unless otherwise specified, and it may, for example, be a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group, a 3,3-dimethylbutyl group, a heptyl group or an octyl group.

The $C_3$-$C_8$ cycloalkyl group represents a cycloalkyl group having a carbon number of from 3 to 8, and it may, for example, be a cyclopropyl group, a cyclobutyl group, a cyclopentyl group or a cyclohexyl group.

The $C_3$-$C_8$ cycloalkyl $C_1$-$C_3$ alkyl group (this group may be substituted by a halogen atom or an alkyl group) represents a $C_1$-$C_3$ alkyl group substituted by a $C_3$-$C_8$ cycloalkyl group which may be substituted by from 1 to 4 halogen atoms or a $C_1$-$C_3$ alkyl group, unless otherwise specified, and it may, for example, be a cyclopropylmethyl group, a 1-cyclopropylethyl group, a 2-cyclopropylethyl group, a 1-cyclopropylpropyl group, a 2-cyclopropylpropyl group, a 3-cyclopropylpropyl group, a cyclobutylmethyl group, a cyclopentylmethyl group, a cyclohexylmethyl group, a 2-chlorocyclopropyl methyl group, a 2,2-dichlorocyclopropylmethyl group, a 2-fluorocyclopropylmethyl group, a 2,2-difluorocyclopropylmethyl group, a 2-methylcyclopropylmethyl group, a 2,2-dimethylcyclopropylmethyl group or a 2-methylcyclopropylethyl group.

The $C_3$-$C_8$ cycloalkyl $C_1$-$C_3$ alkyl group represents an alkyl group having a carbon number of from 1 to 3, substituted by a cycloalkyl group having a carbon number of from 3 to 8, and it may, for example, be a cyclopropylmethyl group, a 1-cyclopropylethyl group, a 2-cyclopropylethyl group, a 1-cyclopropylpropyl group, a 2-cyclopropylpropyl group, a 3-cyclopropylpropyl group, a cyclobutylmethyl group, a cyclopentylmethyl group or a cyclohexylmethyl group.

The $C_1$-$C_4$ haloalkyl group represents a straight chain or branched chain alkyl group having a carbon number of from 1 to 4, independently substituted by from 1 to 9 halogen atoms, unless otherwise specified, and it may, for example, be a fluoromethyl group, a chloromethyl group, a bromomethyl group, a difluoromethyl group, a trifluoromethyl group, a 2,2-difluoroethyl group, a 2,2,2-trifluoroethyl group, or a pentafluoroethyl group.

The $C_2$-$C_6$ alkenyl group represents a straight chain or branched chain alkenyl group having a carbon number of from 2 to 6, and it may, for example, be an ethenyl group, a 1-propenyl group, a 2-propenyl group, an isopropenyl group, a 1-butenyl group, a 2-butenyl group, a 3-butenyl group or a 2-pentenyl group.

The $C_2$-$C_6$ alkynyl group represents a straight chain or branched chain alkynyl group having a carbon number of from 2 to 6, and it may, for example, be an ethynyl group, a 2-propynyl group, a 1-methyl-2-propynyl group, a 2-butynyl group, a 3-butynyl group, or a 2-methyl-3-butynyl group.

The $C_2$-$C_6$ haloalkenyl group represents a straight chain or branched chain alkenyl group having a carbon number of from 2 to 6, independently substituted by from 1 to 4 halogen atoms, unless otherwise specified, and it may, for example, be a 3-chloro-2-propenyl group or a 2-chloro-2-propenyl group.

The $C_1$-$C_{10}$ alkoxy group represents an (alkyl)-O-group wherein the alkyl moiety has the above meaning, and it may, for example, be a methoxy group, an ethoxy group, a n-propoxy group, an isopropoxy group, a tert-butoxy group, a n-butoxy group, a sec-butoxy group or an isobutoxy group.

The $C_1$-$C_4$ haloalkoxy group represents a (haloalkyl)-O-group wherein the haloalkyl moiety has the above meaning, and it may, for example, be a difluoromethoxy group, a trifluoromethoxy group, 2,2-difluoroethoxy group, or a 2,2,2-trifluoroethoxy group.

The $C_3$-$C_8$ cycloalkyloxy group represents a (cycloalkyl)-O-group wherein the cycloalkyl moiety has the above meaning, and it may, for example, be a cyclopropyloxy group, a cyclobutyloxy group, a cyclopentyloxy group, or a cyclohexyloxy group.

The $C_3$-$C_8$ cycloalkyl $C_1$-$C_3$ alkyloxy group represents a (cycloalkylalkyl)-O-group wherein the cycloalkylalkyl moiety has the above meaning, and it may, for example, be a cyclopropylmethoxy group, a 1-cyclopropylethoxy group, a 2-cyclopropylethoxy group, a 1-cyclopropylpropoxy group, a 2-cyclopropylpropoxy group, a 3-cyclopropylpropoxy group, a cyclobutylmethoxy group, a cyclopentylmethoxy group, or a cyclohexylmethoxy group.

The $C_2$-$C_6$ alkenyloxy group and the $C_2$-$C_6$ alkynyloxy group, represent an (alkenyl)-O-group and an (alkynyl)-O-group, wherein the alkenyl or alkynyl moiety has the above meaning, and they may, for example, be a 2-propenyloxy group, and a 2-propynyloxy group, respectively.

The $C_1$-$C_{10}$ alkoxyimino group represents an (alkoxy)-N=group wherein the alkoxy moiety has the above meaning, and it may, for example, be a methoxyimino group or an ethoxyimino group.

The $C_1$-$C_{10}$ alkylthio group, the $C_1$-$C_{10}$ alkylsulfinyl group and the $C_1$-$C_{10}$ alkylsulfonyl group represent an (alkyl)-S-group, an (alkyl)-SO-group and an (alkyl)-$SO_2$-group, wherein the alkyl moiety has the above meaning, and they may, for example, be a methylthio group, an ethylthio group, a n-propylthio group, an isopropylthio group, a methylsulfinyl group, a methylsulfonyl group, an ethylsulfonyl group, a n-propylsulfonyl group, or an isopropylsulfonyl group.

The $C_1$-$C_{10}$ alkylsulfonyloxy group represents an (alkylsulfonyl)-O-group wherein the alkylsulfonyl moiety has the above meaning, and it may, for example, be a methylsulfonyloxy group or an ethylsulfonyloxy group.

The $C_1$-$C_{10}$ alkoxycarbonyl group represents an (alkoxy)-CO-group wherein the alkoxy moiety has the above meaning, and it may, for example, be a methoxycarbonyl group, an ethoxycarbonyl group, a n-propoxycarbonyl group or an isopropoxycabonyl group.

The $C_1$-$C_6$ acyl group represents a straight chain or branched chain aliphatic acyl group having a carbon number of from 1 to 6, and it may, for example, be a formyl group, an acetyl group, a propionyl group, an isopropionyl group, a butyryl group or a pivaloyl group.

The $C_1$-$C_{10}$ acyloxy group represents an (acyl)-O-group wherein the acyl moiety has the above meaning, and it may, for example, be an acetoxy group, a propionyloxy group, an isopropionyloxy group or a pivaloyloxy group.

The $C_1$-$C_4$ haloalkylcarbonyl group, the $C_1$-$C_4$ haloalkylthio group and the $C_1$-$C_4$ haloalkylsulfonyl group represent a (haloalkyl)-CO-group, a (haloalkyl)-S-group and a (haloalkyl)-$SO_2$-group, wherein the haloalkyl moiety has the above meaning, and they may, for example, be a chloroacetyl group, a trifluoroacetyl group, a pentafluoropropionyl group, a difluoromethylthio group, a trifluoromethylthio group, a chloromethylsulfonyl group, a difluoromethylsulfonyl group, or a trifluoromethylsulfonyl group.

The $C_1$-$C_4$ haloalkylcarbonyloxy group and the $C_1$-$C_4$ haloalkylsulfonyloxy group represent a (haloalkylcarbonyl)-O-group and a (haloalkylsulfonyl)-O-group, wherein the haloalkylcarbonyl moiety an the haloalkylsulfonyl moiety have the above meanings, and they may, for example, be a chloroacetyloxy group, a trifluoroacetyloxy group, a chloromethylsulfonyloxy group, or a trifluoromethylsulfonyloxy group, In the phenyl group (which may be substituted), the aromatic heterocyclic group (which may be substituted), the phenoxy group (which may be substituted), the aromatic heterocyclic oxy group (which may be substituted), the phenylthio group (which may be substituted), the aromatic heterocyclic thio group (which may be substituted), the phenylsulfonyl group (which may be substituted), the phenylsulfonyloxy group (which may be substituted), the aromatic heterocyclic sulfonyl group (which may be substituted), the benzylcarbonyl group (which may be substituted), the benzylcarbonyloxy group (which may be substituted), the benzylsulfonyl group (which may be substituted), the benzoyl group (which may be substituted), the benzoyloxy group (which may be substituted), the benzyloxycarbonyl group (which may be substituted) or the phenoxycarbonyl group (which may be substituted), the "group which may be substituted" means that such a group may be substituted by e.g. a halogen atom, a $C_1$-$C_{10}$ alkyl group, a $C_1$-$C_4$ haloalkyl group, a $C_1$-$C_{10}$ alkoxyalkyl group, a $C_1$-$C_{10}$ alkoxy group, a $C_1$-$C_{10}$ alkylthio group, a $C_1$-$C_{10}$ alkylsulfonyl group, a $C_1$-$C_6$ acyl group, a $C_1$-$C_{10}$ alkoxycarbonyl group, a cyano group, a carbamoyl group (the nitrogen atom in the group may be independently substituted by a $C_1$-$C_{10}$ alkyl group), a nitro group or an amino group (the nitrogen atom in the group may be independently substituted by a $C_1$-$C_{10}$ alkyl group, a $C_1$-$C_6$ acyl group, a $C_1$-$C_4$ haloalkylcarbonyl group, a $C_1$-$C_{10}$ alkylsulfonyl group or a $C_1$-$C_4$ haloalkylsulfonyl group).

The 5- or 6-membered aromatic heterocyclic group having an optional hetero atom selected from the group consisting of a nitrogen atom, an oxygen atom and a sulfur atom, may, for example, be a furyl group, a thienyl group, a pyrrolyl group, a pyrazolyl group, an isoxazolyl group, an isothiazolyl group, an oxazolyl group, a thiazolyl group, an imidazolyl group, a pyridyl group, a pyridazinyl group, a pyrimidinyl group, a pyrazinyl group, a triazinyl group, a triazolyl group, an oxadiazolyl group or a thiadiazolyl group, having from 1 to 3 hetero atoms.

The aromatic condensed heterocyclic group represents a group having from 1 to 3 hetero atoms optionally selected from a nitrogen atom, an oxygen atom and a sulfur atom, and it may, for example, be a benzofuryl group, a benzothienyl group, an indolyl group, a benzoxazolyl group, a benzothiazolyl group, a benzoimidazolyl group, a benzoisoxazolyl group, a benzoisothiazolyl group, an indazolyl group, a quinolyl group, an isoquinolyl group, a phthaladinyl group, a quinoxalinyl group, a quinazolinyl group, a cinnolinyl group or a benzotriazolyl group.

The aromatic hetero ring in the aromatic heterocyclic group (which may be substituted), the aromatic heterocyclic oxy group (which may be substituted), the aromatic heterocyclic thio group (which may be substituted), or the aromatic heterocyclic sulfonyl group (which may be substituted), represents a 5- or 6-membered group having from 1 to 3 hetero atoms optionally selected from a nitrogen atom, an oxygen atom and a sulfur atom, and it may, for example, be a furyl group, a thienyl group, a pyrrolyl group, a pyrazolyl group, an isoxazolyl group, an isothiazolyl group, an oxazolyl group, a thiazolyl group, an imidazolyl group, a pyridyl group, a pyridazinyl group, a pyrimidinyl group, a pyrazinyl group, a triazinyl group, a triazolyl group, an oxadiazolyl group or a thiadiazolyl group.

Of a compound of the formula [I] having e.g. a hydroxyl group, a carboxyl group or an amino group in its structure, a pharmacologically acceptable salt is a salt of such a group with a metal or an organic base or a salt with a mineral acid or an organic salt. The metal may be an alkali metal such as sodium or potassium, or an alkaline earth metal such as magnesium or calcium, and the organic base may, for example, be triethylamine or diisopropylamine. The mineral acid may, for example, be hydrochloric acid or sulfuric acid, and the organic acid may, for example, be acetic acid, methanesulfonic acid or p-toluenesulfonic acid.

Now, typical examples of the compound of the formula [I] useful for Component A will be shown in Tables 1 to 14, but the compound is not limited to such examples and may, for example, include compounds exemplified in the above-mentioned Patent Document 1.

The following symbols in the Tables in this specification represent the respective corresponding groups as shown below.

| | |
|---|---|
| Me: Methyl group | Et: Ethyl group |
| Pr: n-Propyl group | Pr-i: Isopropyl group |
| Pr-c: Cyclopropyl group | Bu: n-Butyl group |
| Bu-i: iso-Butyl group | Bu-s: sec-Butyl group |
| Bu-t: tert-Butyl group | Bu-c: Cyclobutyl group |
| Pen: n-Pentyl group | Pen-c: Cyclopentyl group |
| Hex: n-Hexyl group | Hex-c: Cyclohexyl group |
| Ph: Phenyl group | |

Further, for example, (4-Cl)Ph represents a 4-chlorophenyl group, and 3-Hex represents a 3-hexyl group.

Further, in a case where a compound of the present invention contains a hydroxyl group as a substituent, it may have keto-enol tautomers, and the respective tautomers and their mixtures are also included in the compound of the present invention.

TABLE 1

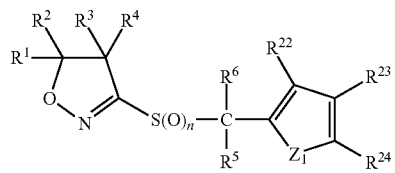

| Compound No. | $R^1$ | $R^2$ | $R^3$ | $R^4$ | n | $R^5$ | $R^6$ | $Z_1$ | $R^{22}$ | $R^{23}$ | $R^{24}$ | m.p. (° C.) or refractive index ($n_D^{20}$) |
|---|---|---|---|---|---|---|---|---|---|---|---|---|
| 1-0001 | Me | Me | H | H | 2 | H | H | S | Me | H | H | 66-68 |
| 1-0002 | Me | Me | H | H | 2 | H | H | S | Cl | Me | H | 87-88 |
| 1-0003 | Me | Me | H | H | 2 | H | H | S | H | H | Me | 95-97 |
| 1-0004 | Me | Me | H | H | 2 | H | H | S | Cl | H | H | 70-72 |
| 1-0005 | Me | Me | H | H | 2 | H | H | S | H | H | Cl | 118-119 |
| 1-0006 | Me | Me | H | H | 2 | H | H | O | H | H | H | Not-measurable |
| 1-0007 | Me | Me | H | H | 2 | H | H | O | H | H | C(=O)OMe | 124-125 |

TABLE 2

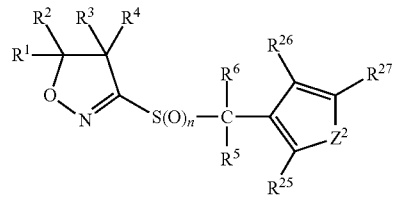

| Compound No. | $R^1$ | $R^2$ | $R^3$ | $R^4$ | n | $R^5$ | $R^6$ | $Z^2$ | $R^{25}$ | $R^{26}$ | $R^{27}$ | m.p. (° C.) or refractive index ($n_D^{20}$) |
|---|---|---|---|---|---|---|---|---|---|---|---|---|
| 2-0001 | Me | Me | H | H | 2 | H | H | S | Me | C(=NOMe)Me | Me | 95-96 |
| 2-0002 | Me | Me | H | H | 0 | H | H | S | Me | C(=NOMe)Me | Me | |
| 2-0003 | Me | Me | H | H | 2 | H | H | S | H | H | H | 99-101 |
| 2-0004 | Me | Me | H | H | 2 | H | H | S | H | OMe | H | 96-97 |
| 2-0005 | Me | Me | H | H | 2 | H | H | S | Cl | H | Cl | 125-127 |
| 2-0006 | Me | Me | H | H | 2 | H | H | S | Cl | Cl | Cl | 158-160 |
| 2-0007 | Me | Me | H | H | 2 | H | H | S | Me | Me | Me | 117-117 |
| 2-0008 | Me | Me | H | H | 2 | H | H | S | Me | C(=O)Me | Me | 146-148 |
| 2-0009 | Me | Me | H | H | 2 | H | H | S | Ph | C(=O)Me | Me | 1.5730 |
| 2-0010 | Me | Me | H | H | 2 | H | H | S | Ph | C(=NOMe)Me | Me | 129-131 |
| 2-0011 | Me | Me | H | H | 2 | H | H | S | Cl | C(=O)OMe | Cl | 157-158 |
| 2-0012 | Me | Me | H | H | 2 | H | H | S | Cl | C(=O)NHMe | Cl | 178-180 |
| 2-0013 | Me | Me | H | H | 2 | H | H | O | H | H | H | 58-61 |
| 2-0014 | Me | Me | H | H | 2 | H | H | O | Me | H | Cl | 180-181 |

TABLE 3

[Structure: isoxazoline ring with R¹, R², R³, R⁴ substituents connected via S(O)ₙ-C(R⁵)(R⁶)- to a pyrazole ring with R²⁹, R²⁸, R³⁰ substituents]

| Compound No. | R¹ | R² | R³ | R⁴ | n | R⁵ | R⁶ | R²⁹ | R²⁸ | R³⁰ | m.p. (° C.) or refractive index ($n_D^{20}$) |
|---|---|---|---|---|---|---|---|---|---|---|---|
| 3-0001 | Me | Me | H | H | 0 | H | H | CF₃ | Ph | Cl | 89-90 |
| 3-0002 | Me | Me | H | H | 2 | H | H | CF₃ | Ph | Cl | 132-133 |
| 3-0003 | Me | Me | H | H | 1 | H | H | Ph | Me | Cl | Not-measurable |
| 3-0004 | Me | Me | H | H | 2 | H | H | CF₃ | Ph | SO₂Et | 158-160 |
| 3-0005 | Me | Me | H | H | 2 | H | H | CF₃ | Ph | N(Me)₂ | 150-151 |
| 3-0006 | Me | Me | H | H | 0 | H | H | CF₃ | Bu-t | Cl | 79-81 |
| 3-0007 | Me | Me | H | H | 0 | H | H | CF₃ | H | Cl | 120-122 |
| 3-0008 | Me | Me | H | H | 0 | H | H | CF₃ | CHF₂ | Cl | 41-42 |
| 3-0009 | Me | Me | H | H | 0 | H | H | Cl | CHF₂ | CF₃ | 89-90 |
| 3-0010 | Me | Me | H | H | 2 | H | H | CF₃ | CHF₂ | Cl | 126-127 |
| 3-0011 | Me | Me | H | H | 2 | H | H | Cl | CHF₂ | CF₃ | 136-137 |
| 3-0012 | Me | Me | H | H | 2 | H | H | OEt | Me | CF₃ | 124-125 |
| 3-0013 | Me | Me | H | H | 2 | H | H | CF₃ | Me | OMe | 113-114 |
| 3-0014 | Me | Me | H | H | 2 | H | H | CF₃ | Me | O (2-Cl)Ph | 67-70 |
| 3-0015 | Me | Me | H | H | 2 | H | H | CF₃ | Me | OPen-c | 113-114 |
| 3-0016 | Me | Me | H | H | 2 | H | H | CF₃ | Me | CN | 105-108 |
| 3-0017 | Me | Me | H | H | 2 | H | H | Cl | Et | Cl | 105-107 |
| 3-0018 | Me | Me | H | H | 2 | H | H | CHF₂ | Me | Cl | 78-79 |
| 3-0019 | Me | Me | H | H | 2 | H | H | CF₃ | —(CH₂)₃O— | | 151-152 |
| 3-0020 | Me | Me | H | H | 0 | H | H | CHF₂ | Me | Cl | 1.5183 |
| 3-0021 | Me | Me | H | H | 0 | H | H | CF₃ | Ph | F | |
| 3-0022 | Me | Me | H | H | 0 | H | H | CF₃ | Ph | SEt | |
| 3-0023 | Me | Me | H | H | 0 | H | H | CF₃ | Ph | N(Me)₂ | |
| 3-0024 | Me | Me | H | H | 0 | H | H | OMe | Me | CF₃ | |
| 3-0025 | Me | Me | H | H | 0 | H | H | OH | Me | CF₃ | |
| 3-0026 | Me | Me | H | H | 0 | H | H | OEt | Me | CF₃ | |
| 3-0027 | Me | Me | H | H | 0 | H | H | CF₃ | Me | F | |
| 3-0028 | Me | Me | H | H | 0 | H | H | CF₃ | Me | OMe | |
| 3-0029 | Me | Me | H | H | 0 | H | H | CF₃ | Me | O (2-Cl)Ph | |
| 3-0030 | Me | Me | H | H | 0 | H | H | CF₃ | Me | OPen-c | |
| 3-0031 | Me | Me | H | H | 0 | H | H | CF₃ | Me | CN | |
| 3-0032 | Me | Me | H | H | 0 | H | H | Cl | Et | Cl | |
| 3-0033 | Me | Me | H | H | 0 | H | H | CF₃ | —(CH₂)₃O— | | |
| 3-0034 | Me | Me | H | H | 2 | H | H | CF₃ | H | Cl | 138-140 |

TABLE 4

| Compound No. | R¹ | R² | R³ | R⁴ | n | R⁵ | R⁶ | R²⁹ | R²⁸ | R³⁰ | m.p.(° C.) or refractive index ($n_D^{20}$) |
|---|---|---|---|---|---|---|---|---|---|---|---|
| 3-0035 | Me | Me | H | H | 2 | H | H | H | Me | Cl | 105-106 |
| 3-0036 | Me | Me | H | H | 2 | H | H | Me | Me | Me | 148-150 |
| 3-0037 | Me | Me | H | H | 2 | H | H | Me | Me | Cl | 99-101 |
| 3-0038 | Me | Me | H | H | 2 | H | H | Cl | Me | Cl | 143-145 |
| 3-0039 | Me | Me | H | H | 2 | H | H | CF₃ | Me | Cl | 115-116 |
| 3-0040 | Me | Me | H | H | 2 | H | H | Cl | Me | CF₃ | 120-122 |
| 3-0041 | Me | Me | H | H | 2 | H | H | CF₃ | Me | F | 79-82 |
| 3-0042 | Me | Me | H | H | 2 | H | H | CF₃ | Me | OH | 90-92 |
| 3-0043 | Me | Me | H | H | 2 | H | H | OMe | Me | CF₃ | 125-126 |
| 3-0044 | Me | Me | H | H | 2 | H | H | CF₃ | Me | OEt | 92-94 |
| 3-0045 | Me | Me | H | H | 2 | H | H | CF₃ | Me | OPr-i | 69-71 |
| 3-0046 | Me | Me | H | H | 2 | H | H | CF₃ | Me | OPr | 82-83 |
| 3-0047 | Me | Me | H | H | 2 | H | H | CF₃ | Me | OBu-t | 86-89 |
| 3-0048 | Me | Me | H | H | 2 | H | H | CF₃ | Me | OBu | 61-62 |
| 3-0049 | Me | Me | H | H | 2 | H | H | CF₃ | Me | OHex-c | 124-125 |
| 3-0050 | Me | Me | H | H | 2 | H | H | CF₃ | Me | OCH₂Pr-c | 93-94 |
| 3-0051 | Me | Me | H | H | 2 | H | H | CF₃ | Me | OCH₂Pen-c | 112-113 |
| 3-0052 | Me | Me | H | H | 2 | H | H | CF₃ | Me | OCH₂Hex-c | 56-59 |
| 3-0053 | Me | Me | H | H | 2 | H | H | CF₃ | Me | OCH₂C≡CH | 92-93 |

TABLE 4-continued

| Compound No. | $R^1$ | $R^2$ | $R^3$ | $R^4$ | n | $R^5$ | $R^6$ | $R^{29}$ | $R^{28}$ | $R^{30}$ | m.p.(° C.) or refractive index ($n_D^{20}$) |
|---|---|---|---|---|---|---|---|---|---|---|---|
| 3-0054 | Me | Me | H | H | 2 | H | H | $CF_3$ | Me | $OCHF_2$ | 129-130 |
| 3-0055 | Me | Me | H | H | 2 | H | H | $OCHF_2$ | Me | $CF_3$ | Not-measurable |
| 3-0056 | Me | Me | H | H | 2 | H | H | $CF_3$ | Me | $OCH_2CHF_2$ | 89-91 |
| 3-0057 | Me | Me | H | H | 2 | H | H | $CF_3$ | Me | $OCH_2CF_3$ | 93-95 |
| 3-0058 | Me | Me | H | H | 2 | H | H | $CF_3$ | Me | $OCH_2CN$ | 1.4872 |
| 3-0059 | Me | Me | H | H | 2 | H | H | $CF_3$ | Me | $OCH_2Ph$ | 79-81 |
| 3-0060 | Me | Me | H | H | 2 | H | H | $CF_3$ | Me | OPh | 122-123 |
| 3-0061 | Me | Me | H | H | 2 | H | H | $CF_3$ | Me | O(3-Cl)Ph | Not-measurable |
| 3-0062 | Me | Me | H | H | 2 | H | H | $CF_3$ | Me | O(3-OMe)Ph | 1.5059 |
| 3-0063 | Me | Me | H | H | 2 | H | H | $CF_3$ | Me | O(4-Cl)Ph | 68-69 |
| 3-0064 | Me | Me | H | H | 2 | H | H | $CF_3$ | Me | O(4-Me)Ph | 132-133 |
| 3-0065 | Me | Me | H | H | 2 | H | H | $CF_3$ | Me | O(4-OMe)Ph | 115-117 |
| 3-0066 | Me | Me | H | H | 2 | H | H | $CF_3$ | Me | OC(=O)Me | 130-131 |
| 3-0067 | Me | Me | H | H | 2 | H | H | $CF_3$ | Me | $SO_2Me$ | 168-169 |
| 3-0068 | Me | Me | H | H | 2 | H | H | $CF_3$ | Me | SEt | 100-102 |
| 3-0069 | Me | Me | H | H | 2 | H | H | $CF_3$ | Me | $SO_2Et$ | 107-108 |
| 3-0070 | Me | Me | H | H | 2 | H | H | $CF_3$ | Me | $SO_2Ph$ | 166-168 |
| 3-0071 | Me | Me | H | H | 2 | H | H | $CF_3$ | Me | Me | 105-107 |
| 3-0072 | Me | Me | H | H | 2 | H | H | Ph | Me | Cl | 127-129 |

TABLE 5

| Compound No. | $R^1$ | $R^2$ | $R^3$ | $R^4$ | n | $R^5$ | $R^6$ | $R^{29}$ | $R^{28}$ | $R^{30}$ | m.p.(° C.) or refractive index ($n_D^{20}$) |
|---|---|---|---|---|---|---|---|---|---|---|---|
| 3-0073 | Me | Me | H | H | 2 | H | H | $CF_3$ | Et | Cl | 111-112 |
| 3-0074 | Me | Me | H | H | 2 | H | H | Cl | Et | $CF_3$ | 112-114 |
| 3-0075 | Me | Me | H | H | 2 | H | H | $CF_3$ | Pr-i | Cl | 157-158 |
| 3-0076 | Me | Me | H | H | 2 | H | H | Cl | Pr-i | $CF_3$ | 135-136 |
| 3-0077 | Me | Me | H | H | 2 | H | H | $CF_3$ | Pr | Cl | 89-90 |
| 3-0078 | Me | Me | H | H | 2 | H | H | Cl | Pr | $CF_3$ | 111-113 |
| 3-0079 | Me | Me | H | H | 2 | H | H | $CF_3$ | Bu-t | H | 101-103 |
| 3-0080 | Me | Me | H | H | 2 | H | H | $CF_3$ | Bu-t | Cl | 118-119 |
| 3-0081 | Me | Me | H | H | 2 | H | H | $CF_3$ | Bu-s | Cl | 110-112 |
| 3-0082 | Me | Me | H | H | 2 | H | H | Cl | Bu-s | $CF_3$ | 110-111 |
| 3-0083 | Me | Me | H | H | 2 | H | H | $CF_3$ | Bu-i | Cl | 96-98 |
| 3-0084 | Me | Me | H | H | 2 | H | H | Cl | Bu-i | $CF_3$ | 140-141 |
| 3-0085 | Me | Me | H | H | 2 | H | H | $CF_3$ | Bu | Cl | 89-90 |
| 3-0086 | Me | Me | H | H | 2 | H | H | Cl | Bu | $CF_3$ | 108-110 |
| 3-0087 | Me | Me | H | H | 2 | H | H | $CF_3$ | $CH_2Ph$ | Cl | 132-133 |
| 3-0088 | Me | Me | H | H | 2 | H | H | Cl | $CH_2Ph$ | $CF_3$ | 118-120 |
| 3-0089 | Me | Me | H | H | 2 | H | H | $CF_3$ | Pen-c | Cl | 130-131 |
| 3-0090 | Me | Me | H | H | 2 | H | H | Cl | Pen-c | $CF_3$ | 147-148 |
| 3-0091 | Me | Me | H | H | 2 | H | H | $CF_3$ | Hex-c | Cl | 151-152 |
| 3-0092 | Me | Me | H | H | 2 | H | H | $CF_3$ | $CH_2Pr$-c | Cl | 93-95 |
| 3-0093 | Me | Me | H | H | 2 | H | H | Cl | $CH_2Pr$-c | $CF_3$ | 129-130 |
| 3-0094 | Me | Me | H | H | 2 | H | H | $CF_3$ | 1-cyclopropylethyl | Cl | 87-89 |
| 3-0095 | Me | Me | H | H | 2 | H | H | Cl | 1-cyclopropylethyl | $CF_3$ | 121-123 |
| 3-0096 | Me | Me | H | H | 2 | H | H | $CF_3$ | $CH_2$(2-Methylcyclopropyl) | Cl | 102-103 |
| 3-0097 | Me | Me | H | H | 2 | H | H | Cl | $CH_2$(2-Methylcyclopropyl) | $CF_3$ | 118-119 |
| 3-0098 | Me | Me | H | H | 2 | H | H | $CF_3$ | $CH_2Bu$-c | Cl | 94-96 |
| 3-0099 | Me | Me | H | H | 2 | H | H | Cl | $CH_2Bu$-c | $CF_3$ | 141-142 |
| 3-0100 | Me | Me | H | H | 2 | H | H | $CF_3$ | $CH_2Pen$-c | Cl | 127-129 |
| 3-0101 | Me | Me | H | H | 2 | H | H | Cl | $CH_2Pen$-c | $CF_3$ | 146-149 |
| 3-0102 | Me | Me | H | H | 2 | H | H | $CF_3$ | $CH_2Hex$-c | Cl | 152-154 |
| 3-0103 | Me | Me | H | H | 2 | H | H | Cl | $CH_2Hex$-c | $CF_3$ | 115-117 |
| 3-0104 | Me | Me | H | H | 2 | H | H | $CF_3$ | $CH_2CH=CH_2$ | Cl | 78-80 |
| 3-0105 | Me | Me | H | H | 2 | H | H | Cl | $CH_2CH=CH_2$ | $CF_3$ | 105-106 |
| 3-0106 | Me | Me | H | H | 2 | H | H | $CF_3$ | $CH_2C\equiv CH$ | Cl | 73-74 |
| 3-0107 | Me | Me | H | H | 2 | H | H | Cl | $CH_2C\equiv CH$ | $CF_3$ | 108-109 |
| 3-0108 | Me | Me | H | H | 2 | H | H | $CF_3$ | $CHMeC\equiv CH$ | Cl | 95-96 |
| 3-0109 | Me | Me | H | H | 2 | H | H | Cl | $CHMeC\equiv CH$ | $CF_3$ | 116-118 |
| 3-0110 | Me | Me | H | H | 2 | H | H | $CF_3$ | $CH_2C\equiv CMe$ | Cl | 114-115 |

TABLE 6

| Compound No. | R¹ | R² | R³ | R⁴ | n | R⁵ | R⁶ | R²⁹ | R²⁸ | R³⁰ | m.p.(° C.) or refractive index ($n_D^{20}$) |
|---|---|---|---|---|---|---|---|---|---|---|---|
| 3-0111 | Me | Me | H | H | 2 | H | H | Cl | CH₂C≡CMe | CF₃ | 115-116 |
| 3-0112 | Me | Me | H | H | 2 | H | H | CF₃ | CHF₂ | OMe | 72-74 |
| 3-0113 | Me | Me | H | H | 2 | H | H | OMe | CHF₂ | CF₃ | 108-109 |
| 3-0114 | Me | Me | H | H | 2 | H | H | CF₃ | CH₂CHF₂ | Cl | 99-100 |
| 3-0115 | Me | Me | H | H | 2 | H | H | Cl | CH₂CHF₂ | CF₃ | 107-109 |
| 3-0116 | Me | Me | H | H | 2 | H | H | CF₃ | CH₂CF₃ | Cl | 135-136 |
| 3-0117 | Me | Me | H | H | 2 | H | H | Cl | CH₂CF₃ | CF₃ | 112-115 |
| 3-0118 | Me | Me | H | H | 2 | H | H | CF₃ | CH₂OMe | Cl | 87-89 |
| 3-0119 | Me | Me | H | H | 2 | H | H | Cl | CH₂OMe | CF₃ | 125-128 |
| 3-0120 | Me | Me | H | H | 2 | H | H | CF₃ | CH₂OEt | Cl | 97-98 |
| 3-0121 | Me | Me | H | H | 2 | H | H | Cl | CH₂OEt | CF₃ | 128-129 |
| 3-0122 | Me | Me | H | H | 2 | H | H | CF₃ | CH₂CH₂OH | Cl | 79-81 |
| 3-0123 | Me | Me | H | H | 2 | H | H | Cl | CH₂CH₂OH | CF₃ | 93-94 |
| 3-0124 | Me | Me | H | H | 2 | H | H | CF₃ | CH₂CH₂OMe | Cl | 102-104 |
| 3-0125 | Me | Me | H | H | 2 | H | H | Cl | CH₂CH₂OMe | CF₃ | 118-119 |
| 3-0126 | Me | Me | H | H | 2 | H | H | CF₃ | CH₂CH₂OEt | Cl | 56-59 |
| 3-0127 | Me | Me | H | H | 2 | H | H | Cl | CH₂CH₂OEt | CF₃ | 118-119 |
| 3-0128 | Me | Me | H | H | 2 | H | H | CF₃ | CH₂SMe | Cl | 103-105 |
| 3-0129 | Me | Me | H | H | 2 | H | H | Cl | CH₂SMe | CF₃ | 128-129 |
| 3-0130 | Me | Me | H | H | 2 | H | H | CF₃ | CH₂SO₂Me | Cl | 157-159 |
| 3-0131 | Me | Me | H | H | 2 | H | H | Cl | CH₂SO₂Me | CF₃ | 165-166 |
| 3-0132 | Me | Me | H | H | 2 | H | H | CF₃ | CH₂CH₂SO₂Me | Cl | 155-157 |
| 3-0133 | Me | Me | H | H | 2 | H | H | Cl | CH₂CH₂SO₂Me | CF₃ | 166-168 |
| 3-0134 | Me | Me | H | H | 2 | H | H | CF₃ | CH₂CN | Cl | 128-129 |
| 3-0135 | Me | Me | H | H | 2 | H | H | Cl | CH₂CN | CF₃ | 117-118 |
| 3-0136 | Me | Me | H | H | 2 | H | H | CF₃ | CH₂C(=O)OEt | Cl | 127-129 |
| 3-0137 | Me | Me | H | H | 2 | H | H | Cl | CH₂C(=O)OEt | CF₃ | 143-145 |
| 3-0138 | Me | Me | H | H | 2 | H | H | CF₃ | CH₂C(=O)NH₂ | Cl | 173-174 |
| 3-0139 | Me | Me | H | H | 2 | H | H | Cl | CH₂C(=O)NH₂ | CF₃ | 182-183 |
| 3-0140 | Me | Me | H | H | 2 | H | H | CF₃ | CH₂C(=O)N(Me)₂ | Cl | 142-143 |
| 3-0141 | Me | Me | H | H | 2 | H | H | Cl | CH₂C(=O)N(Me)₂ | CF₃ | 181-182 |
| 3-0142 | Me | Me | H | H | 2 | H | H | CF₃ | CH₂C(=O)Me | Cl | 148-149 |
| 3-0143 | Me | Me | H | H | 2 | H | H | Cl | CH₂C(=O)Me | CF₃ | 163-164 |
| 3-0144 | Me | Me | H | H | 2 | H | H | CF₃ | CH₂CH₂C(=O)Me | Cl | 89-91 |
| 3-0145 | Me | Me | H | H | 2 | H | H | Me | Ph | Me | 140-141 |
| 3-0146 | Me | Me | H | H | 2 | H | H | Me | Ph | Cl | 124-125 |
| 3-0147 | Me | Me | H | H | 2 | H | H | Et | Ph | Cl | 112-113 |
| 3-0148 | Me | Me | H | H | 2 | H | H | Pr | Ph | Cl | 122-123 |

TABLE 7

| Compound No. | R¹ | R² | R³ | R⁴ | n | R⁵ | R⁶ | R²⁹ | R²⁸ | R³⁰ | m.p.(° C.) or refractive index ($n_D^{20}$) |
|---|---|---|---|---|---|---|---|---|---|---|---|
| 3-0149 | Me | Me | H | H | 2 | H | H | Pr-i | Ph | Cl | 116-117 |
| 3-0150 | Me | Me | H | H | 2 | H | H | Bu-t | Ph | Cl | 100-102 |
| 3-0151 | Me | Me | H | H | 2 | H | H | CF₃ | Ph | H | 111-112 |
| 3-0152 | Me | Me | H | H | 2 | H | H | CF₃ | Ph | Me | 129-132 |
| 3-0153 | Me | Me | H | H | 2 | H | H | CF₃ | Ph | CF₃ | 112-113 |
| 3-0154 | Me | Me | H | H | 2 | H | H | CF₃ | Ph | F | 90-91 |
| 3-0155 | Me | Me | H | H | 2 | H | H | CF₃ | Ph | OMe | 104-106 |
| 3-0156 | Me | Me | H | H | 2 | H | H | CF₃ | Ph | OEt | 129-131 |
| 3-0157 | Me | Me | H | H | 2 | H | H | CF₃ | Ph | OPr-i | 86-88 |
| 3-0158 | Me | Me | H | H | 2 | H | H | CF₃ | Ph | OPr | 117-118 |
| 3-0159 | Me | Me | H | H | 2 | H | H | CF₃ | Ph | OBu-t | 105-108 |
| 3-0160 | Me | Me | H | H | 2 | H | H | CF₃ | Ph | OCHF₂ | 90-92 |
| 3-0161 | Me | Me | H | H | 2 | H | H | CF₃ | Ph | SO₂Me | 167-168 |
| 3-0162 | Me | Me | H | H | 2 | H | H | CF₃ | Ph | CN | 113-115 |
| 3-0163 | Me | Me | H | H | 2 | H | H | CF₃ | (2-Cl)Ph | Cl | 153-154 |
| 3-0164 | Me | Me | H | H | 2 | H | H | CF₃ | (3-Cl)Ph | Cl | 106-107 |
| 3-0165 | Me | Me | H | H | 2 | H | H | CF₃ | (4-Cl)Ph | Cl | 142-143 |
| 3-0166 | Me | Me | H | H | 2 | H | H | CF₃ | (4-F)Ph | Cl | 135-138 |
| 3-0167 | Me | Me | H | H | 2 | H | H | CF₃ | (4-OMe)Ph | Cl | 136-138 |
| 3-0168 | Me | Me | H | H | 2 | H | H | CF₃ | (4-Me)Ph | Cl | 129-130 |
| 3-0169 | Me | Me | H | H | 2 | H | H | CF₃ | (4-NO₂)Ph | Cl | 145-147 |
| 3-0170 | Me | Me | H | H | 2 | H | H | CF₃ | (4-CN)Ph | Cl | 91-93 |
| 3-0171 | Me | Me | H | H | 2 | H | H | CF₃ | (4-C(=O)Me)Ph | Cl | 133-135 |
| 3-0172 | Me | Me | H | H | 2 | H | H | CF₃ | (4-C(=O)OMe)Ph | Cl | 121-124 |
| 3-0173 | Me | Me | H | H | 2 | H | H | CF₃ | Pyrmidin-2-yl | Cl | 148-150 |
| 3-0174 | Me | Me | H | H | 2 | H | H | CF₃ | 4,6-Dimethoxypyrmidin- | Cl | 117-118 |

TABLE 7-continued

| Compound No. | R¹ | R² | R³ | R⁴ | n | R⁵ | R⁶ | R²⁹ | R²⁸ | R³⁰ | m.p.(° C.) or refractive index ($n_D^{20}$) |
|---|---|---|---|---|---|---|---|---|---|---|---|
| 3-0175 | Me | Me | H | H | 2 | H | H | CF₃ | SO₂Me 2-yl | Cl | 146-148 |
| 3-0176 | Me | Me | H | H | 2 | H | H | CF₃ | SO₂Ph | Cl | 145-148 |
| 3-0177 | Me | Me | H | H | 2 | H | H | CF₃ | C(=O)Me | Cl | 130-131 |
| 3-0178 | Me | Me | H | H | 2 | H | H | CF₃ | C(=O)Ph | Cl | 114-117 |
| 3-0179 | Me | Me | H | H | 2 | H | H | CF₃ | C(=O)OMe | Cl | 104-106 |
| 3-0180 | Me | Et | H | H | 2 | H | H | CF₃ | Me | Cl | 108-110 |
| 3-0181 | Me | Me | H | H | 0 | H | H | CHF₂ | Me | Cl | 1.5183 |
| 3-0182 | Me | Me | H | H | 0 | H | H | Ph | Me | Cl | 76-77 |
| 3-0183 | Me | Me | H | H | 0 | H | H | CF₃ | Bu-t | OMe | 1.4831 |
| 3-0184 | Me | Me | H | H | 0 | H | H | CF₃ | CH₂C(=O)NH₂ | Cl | 179-180 |
| 3-0185 | Me | Me | H | H | 0 | H | H | Me | Ph | Cl | 58-60 |
| 3-0186 | Me | Me | H | H | 0 | H | H | CF₃ | Me | Cl | |
| 3-0187 | Me | Me | H | H | 0 | H | H | CF₃ | Me | OCHF₂ | |
| 3-0188 | Me | Me | H | H | 2 | H | H | CF₃ | Me | OCHF₂ | 129-130 |
| 3-0189 | Me | Me | H | H | 0 | H | H | CF₃ | Et | OCHF₂ | |
| 3-0190 | Me | Me | H | H | 2 | H | H | CF₃ | Et | OCHF₂ | 98-100 |

TABLE 8

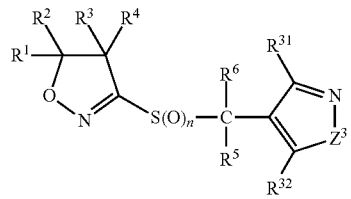

| Compound No. | R¹ | R² | R³ | R⁴ | n | R⁵ | R⁶ | Z³ | R³¹ | R³² | m.p. (° C.) or refractive index ($n_D^{20}$) |
|---|---|---|---|---|---|---|---|---|---|---|---|
| 4-0001 | Me | Me | H | H | 2 | H | H | O | CF₃ | Me | 135-136 |
| 4-0002 | Me | Me | H | H | 2 | H | H | S | Me | Cl | 113-114 |
| 4-0003 | Me | Me | H | H | 0 | H | H | O | CF₃ | Me | |
| 4-0004 | Me | Me | H | H | 0 | H | H | S | Me | Cl | |
| 4-0005 | Me | Me | H | H | 2 | H | H | O | Me | Me | 178-179 |
| 4-0006 | Me | Me | H | H | 2 | H | H | O | CF₃ | OEt | 89-91 |
| 4-0007 | Me | Me | H | H | 2 | H | H | O | Ph | Me | 81-83 |
| 4-0008 | Me | Me | H | H | 2 | H | H | O | Me | OEt | 109-111 |

TABLE 9

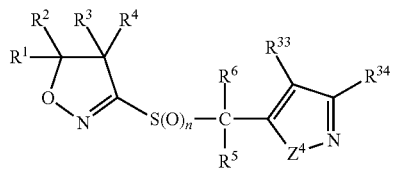

| Compound No. | R¹ | R² | R³ | R⁴ | n | R⁵ | R⁶ | Z⁴ | R³³ | R³⁴ | m.p. (° C.) or refractive index ($n_D^{20}$) |
|---|---|---|---|---|---|---|---|---|---|---|---|
| 5-0001 | Me | Me | H | H | 2 | H | H | NMe | Cl | Me | 114-115 |
| 5-0002 | Me | Me | H | H | 2 | H | H | NMe | Cl | Et | 107-108 |
| 5-0003 | Me | Me | H | H | 2 | H | H | NMe | CF₃ | H | 142-143 |
| 5-0004 | Me | Me | H | H | 2 | H | H | NCHF₂ | —(CH₂)₄— | | 123-125 |
| 5-0005 | Me | Me | H | H | 2 | H | H | NPh | OEt | Me | 1.5397 |
| 5-0006 | Me | Me | H | H | 2 | H | H | NPh | OCHF₂ | Me | 1.5339 |
| 5-0007 | Me | Me | H | H | 2 | H | H | NPh | CF₃ | H | 99-101 |
| 5-0008 | Me | Me | H | H | 2 | H | H | NPh | OCH₂CH=CH₂ | Me | 87-90 |
| 5-0009 | Me | Me | H | H | 1 | H | H | NPh | OCH₂CH=CH₂ | Me | 1.5702 |

TABLE 10

[Structure: isoxazoline with R¹, R², R³, R⁴ substituents connected via S(O)ₙ-C(R⁵)(R⁶) to a heterocycle with R³⁵, R³⁶, Z⁵]

| Compound No. | R¹ | R² | R³ | R⁴ | n | R⁵ | R⁶ | Z⁵ | R³⁵ | R³⁶ | m.p. (°C.) or refractive index ($n_D^{20}$) |
|---|---|---|---|---|---|---|---|---|---|---|---|
| 6-0001 | Me | Me | H | H | 2 | H | H | NCHF₂ | —(CH₂)₄— | | Not-measurable |
| 6-0002 | Me | Me | H | H | 2 | H | H | NPh | H | OEt | 107-108 |
| 6-0003 | Me | Me | H | H | 2 | H | H | NPh | H | OCHF₂ | 1.5383 |
| 6-0004 | Me | Me | H | H | 2 | H | H | O | Me | H | 100-102 |
| 6-0005 | Me | Me | H | H | 0 | H | H | NCHF₂ | —(CH₂)₄— | | 1.5264 |

TABLE 11

[Structure: isoxazoline-S(O)ₙ-C(R⁵)(R⁶)- pyridine with R³⁷, R³⁸, R³⁹, R⁴⁰ and optional N-oxide]

| Compound No. | R¹ | R² | R³ | R⁴ | n | R⁵ | R⁶ | R³⁷ | R³⁸ | R³⁹ | R⁴⁰ | | m.p. (°C.) or refractive index ($n_D^{20}$) |
|---|---|---|---|---|---|---|---|---|---|---|---|---|---|
| 7-0001 | Me | Me | H | H | 2 | H | H | H | CF₃ | H | H | — | 77-80 |
| 7-0002 | Me | Me | H | H | 2 | H | H | H | CF₃ | H | H | N-oxide | 114-116 |
| 7-0003 | Me | Me | H | H | 0 | H | H | H | CF₃ | H | H | — | |
| 7-0004 | Me | Me | H | H | 2 | H | H | H | H | H | H | — | 130-131 |
| 7-0005 | Me | Me | H | H | 2 | H | H | H | H | H | H | N-oxide | 166-168 |
| 7-0006 | Me | Me | H | H | 2 | H | H | Cl | Ph | H | H | — | 118-120 |
| 7-0007 | Me | Me | H | H | 2 | H | H | OMe | Ph | H | H | — | 105-106 |
| 7-0008 | Me | Me | H | H | 2 | H | H | Cl | Me | H | H | — | 115-116 |
| 7-0009 | Me | Me | H | H | 2 | H | H | OMe | Me | H | H | — | 134-135 |
| 7-0010 | Me | Me | H | H | 2 | H | H | Me | Me | H | H | N-oxide | 198-199 |
| 7-0011 | Me | Me | H | H | 2 | H | H | Ph | Ph | H | H | — | 161-162 |
| 7-0012 | Me | Me | H | H | 1 | H | H | H | H | H | H | — | 97-99 |
| 7-0013 | Me | Me | H | H | 0 | H | H | (2-Chloropyridin-3-yl)methylthio | H | H | H | — | 154-155 |

TABLE 12

[Structure: isoxazoline-S(O)ₙ-C(R⁵)(R⁶)- pyrimidine with R⁴¹, R⁴², R⁴³]

| Compound No. | R¹ | R² | R³ | R⁴ | n | R⁵ | R⁶ | R⁴¹ | R⁴² | R⁴³ | m.p. (°C.) or refractive index ($n_D^{20}$) |
|---|---|---|---|---|---|---|---|---|---|---|---|
| 8-0001 | Me | Me | H | H | 2 | H | H | H | OMe | CF₃ | 175-176 |
| 8-0002 | Me | Me | H | H | 0 | H | H | H | OMe | CF₃ | |
| 8-0003 | Me | Me | H | H | 2 | H | H | H | Cl | Cl | 119-120 |
| 8-0004 | Me | Me | H | H | 2 | H | H | H | OEt | CF₃ | 94-95 |
| 8-0005 | Me | Me | H | H | 2 | H | H | H | OMe | OMe | 186-187 |
| 8-0006 | Me | Me | H | H | 2 | H | H | Me | OMe | CF₃ | 143-144 |

TABLE 12-continued

| Compound No. | R¹ | R² | R³ | R⁴ | n | R⁵ | R⁶ | R⁴¹ | R⁴² | R⁴³ | m.p. (° C.) or refractive index ($n_D^{20}$) |
|---|---|---|---|---|---|---|---|---|---|---|---|
| 8-0007 | Me | Me | H | H | 2 | H | H | OMe | OMe | CF₃ | 144-145 |
| 8-0008 | Me | Me | H | H | 2 | H | H | SMe | OMe | CF₃ | 160-162 |
| 8-0009 | Me | Me | H | H | 2 | H | H | SO₂Me | OMe | CF₃ | 144-146 |
| 8-0010 | Me | Me | H | H | 2 | H | H | NH₂ | OMe | CF₃ | 208-209 |
| 8-0011 | Me | Me | H | H | 2 | Pr-i | H | H | H | CF₃ | 112-113 |
| 8-0012 | Me | Me | H | H | 0 | Pr-i | H | H | H | CF₃ | 1.4986 |

TABLE 13

| Compound No. | R¹ | R² | R³ | R⁴ | n | R⁵ | R⁶ | Y¹ | m.p. (° C.) or refractive index ($n_D^{20}$) |
|---|---|---|---|---|---|---|---|---|---|
| 9-0001 | Me | Me | H | H | 2 | H | H | Pyridin-2-yl | 116-118 |
| 9-0002 | Me | Me | H | H | 2 | H | H | Pyridin-2-yl 1-oxide | 140-143 |
| 9-0003 | Me | Me | H | H | 2 | H | H | Pyridin-4-yl | 133-136 |
| 9-0004 | Me | Me | H | H | 2 | H | H | Pyridin-4-yl 1-oxide | 110-113 |
| 9-0005 | Me | Me | H | H | 2 | H | H | 1,2,4-Oxadiazol-3-yl | Not-measurable |
| 9-0006 | Me | Me | H | H | 2 | H | H | 3-Phenyl-1,2,4-oxadiazol-5-yl | 153-154 |
| 9-0007 | Me | Me | H | H | 2 | H | H | 3-Benzyl-1,2,4-oxadiazol-5-yl | 108-109 |
| 9-0008 | Me | Me | H | H | 2 | H | H | 2-Chloro-thiazol-4-yl | 110-112 |
| 9-0009 | Me | Me | H | H | 2 | H | H | 1,4-Dimethyl-imidazol-5-yl | 163-164 |
| 9-0010 | Me | Me | H | H | 1 | H | H | Pyridin-2-yl | 81-82 |
| 9-0011 | Me | Me | H | H | 1 | H | H | Pyridin-4-yl | 94-96 |
| 9-0012 | Me | Me | H | H | 1 | H | H | 1,4-Dimethyl-imidazol-5-yl | 138-140 |
| 9-0013 | Me | Me | H | H | 0 | H | H | 1,4-Dimethyl-imidazol-5-yl | 1.5427 |

TABLE 14

| Compound No. | R¹ | R² | R³ | R⁴ | n | R⁵ | R⁶ | Y¹ | m.p. (° C.) or refractive index ($n_D^{20}$) |
|---|---|---|---|---|---|---|---|---|---|
| 10-0001 | Me | Me | H | H | 2 | H | H | Benzimidazol-2-yl | 171-174 |
| 10-0002 | Me | Me | H | H | 2 | H | H | Benzothiophen-2-yl | 181-183 |
| 10-0003 | Me | Me | H | H | 2 | H | H | 3-Chloro-benzothiophen-2-yl | 109-112 |
| 10-0004 | Me | Me | H | H | 2 | H | H | Benzotriazol-1-yl | 206-207 |
| 10-0005 | Me | Me | H | H | 2 | H | H | 1-Methylindazol-4-yl | 128-130 |
| 10-0006 | Me | Me | H | H | 2 | H | H | Benzothiazol-2-yl | 142-143 |
| 10-0007 | Me | Me | H | H | 2 | H | H | Benzothiophen-3-yl | 188-191 |
| 10-0008 | Me | Me | H | H | 2 | H | H | 5-Chloro-benzothiophen-3-yl | 129-130 |
| 10-0009 | Me | Me | H | H | 2 | H | H | Benzoxazol-2-yl | 127-129 |
| 10-0010 | Me | Me | H | H | 2 | H | H | 3-Methyl-benzothiophen-2-yl | 161-163 |
| 10-0011 | Me | Me | H | H | 2 | H | H | 3-Bromo-benzothiophen-2-yl | 118-119 |
| 10-0012 | Me | Me | H | H | 2 | H | H | Benzofuran-2-yl | 123-124 |
| 10-0013 | Me | Me | H | H | 2 | H | H | 2-Methyl-benzofuran-7-yl | 135-137 |
| 10-0014 | Me | Me | H | H | 2 | H | H | 3-Bromo-benzofuran-2-yl | 107-108 |
| 10-0015 | Me | Me | H | H | 2 | H | H | Benzothiophen-7-yl | 95-97 |
| 10-0016 | Me | Me | H | H | 2 | H | H | 1-Methylindazol-7-yl | 89-90 |
| 10-0017 | Me | Me | H | H | 2 | H | H | 3-Methyl-benzofuran-2-yl | 111-112 |

TABLE 14-continued

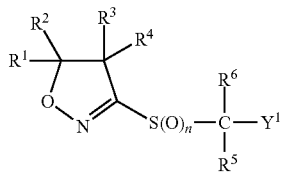

| Compound No. | R$^1$ | R$^2$ | R$^3$ | R$^4$ | n | R$^5$ | R$^6$ | Y$^1$ | m.p. (° C.) or refractive index (n$_D^{20}$) |
|---|---|---|---|---|---|---|---|---|---|
| 10-0018 | Me | Me | H | H | 2 | H | H | 3-Chloro-1-methylindol-2-yl | 162-165 |

In the formula [I] for Component A, preferred is an isoxazoline derivative or its salt, wherein each of R$^1$ and R$^2$ which are independent of each other, is a methyl group or an ethyl group;

each of R$^3$, R$^4$, R$^5$ and R$^6$ is a hydrogen atom; n is an integer of 2;

Y is a thiophen-3-yl group (this group is necessarily substituted at the 2- and 4-positions by a halogen atom, an alkyl group, a haloalkyl group, an alkoxyalkyl group, a cycloalkyl group, an alkoxy group, a haloalkoxy group, an acyl group, a haloalkylcarbonyl group, an alkoxycarbonyl group, a cyano group or a carbamoyl group (the nitrogen atom of this group may independently be substituted by an alkyl group)), a pyrazol-4-yl group (this group is necessarily substituted at the 3- an 5-positions by a halogen atom, an alkyl group, a haloalkyl group, an alkoxyalkyl group, a cycloalkyl group, an alkoxy group, a haloalkoxy group, a cycloalkylalkyloxy group, a phenoxy group which may be substituted, an alkylthio group, an alkylsulfonyl group, an acyl group, a haloalkylcarbonyl group, an alkoxycarbonyl group, a cyano group or a carbamoyl group (the nitrogen atom of this group may independently be substituted by an alkyl group) and further at the 1-position by a hydrogen atom, an alkyl group, an alkyl group mono-substituted by an optional group selected from the substituent group β, a haloalkyl group, a cycloalkyl group, an alkenyl group, an alkynyl group, an alkylsulfonyl group, an alkylsulfonyl group mono-substituted by an optional group selected from the substituent group γ, a haloalkylsulfonyl group, a phenyl group which may be substituted, an aromatic heterocyclic group which may be substituted, a phenylsulfonyl group which may be substituted, an aromatic heterocyclic sulfonyl group which may be substituted, an acyl group, a haloalkylcarbonyl group, a benzylcarbonyl group which may be substituted, a benzoyl group which may be substituted, an alkoxycarbonyl group, a benzyloxycarbonyl group which may be substituted, a phenoxycarbonyl group which may be substituted, or a carbamoyl group (the nitrogen atom of this group may independently be substituted by an alkyl group or a phenyl group which may be substituted)), a pyrazol-5-yl group (this group is necessarily substituted at the 4-position by a halogen atom, an alkyl group, a haloalkyl group, an alkoxyalkyl group, a haloalkoxy group, an acyl group, a haloalkylcarbonyl group, an alkoxycarbonyl group, a cyano group or a carbamoyl group (the nitrogen atom of this group may independently be substituted by an alkyl group) and further at the 1-position by a hydrogen atom, an alkyl group, an alkyl group mono-substituted by an optional group selected from the substituent group β, a haloalkyl group, a cycloalkyl group, or a phenyl group which may be substituted), an isoxazol-4-yl group (this group is necessarily substituted at the 3- and 5-positions, by a halogen atom, an alkyl group, a haloalkyl group, an alkoxyalkyl group, a cycloalkyl group, an alkoxy group, a haloalkoxy group, an alkylthio group, an alkylsulfonyl group, an acyl group, a haloalkylcarbonyl group, an alkoxycarbonyl group, a cyano group, or a carbamoyl group (the nitrogen atom of this group may independently be substituted by an alkyl group)), an isothiazol-4-yl group (this group is necessarily substituted at the 3- and 5-positions by a halogen atom, an alkyl group, a haloalkyl group, an alkoxyalkyl group, a cycloalkyl group, an alkoxy group, a haloalkoxy group, a phenoxy group which may be substituted, an alkylthio group, an alkylsulfonyl group, an acyl group, a haloalkylcarbonyl group, an alkoxycarbonyl group, a cyano group, or a carbamoyl group (the nitrogen atom of this group may independently be substituted by an alkyl group)), a pyridin-3-yl group (this group is necessarily substituted at the 2- and 4-positions, by a halogen atom, an alkyl group, a haloalkyl group, an alkoxyalkyl group, a cycloalkyl group, an alkoxy group, a haloalkoxy group, an alkylthio group, an alkylsulfonyl group, an acyl group, a haloalkylcarbonyl group, an alkoxycarbonyl group, a cyano group, or a carbamoyl group (the nitrogen atom of this group may independently be substituted by an alkyl group)), or a pyrimidin-5-yl group (this group is necessarily substituted at the 4- and 6-positions by a halogen atom, an alkyl group, a haloalkyl group, an alkoxyalkyl group, a cycloalkyl group, an alkoxy group, a haloalkoxy group, an alkylthio group, an alkylsulfonyl group, an acyl group, a haloalkylcarbonyl group, an alkoxycarbonyl group, a cyano group, or a carbamoyl group (the nitrogen atom of this group may independently be substituted by an alkyl group)).

A herbicidal compound particularly preferred as Component A is Compound No. 3-0054.

The compound represented by the formula [I] can be produced by the method disclosed in Patent Document 1 or methods in accordance therewith.

Whereas herbicidal compounds preferred as Component B are quizalofop-P-ethyl, sethoxydim, pyrithiobac-sodium, bispyribac-sodium, pyrimisulfan, imazethapyr, imazaquin, chlorimuron-ethyl, diuron, bentazone, paraquat, sulfentrazone, fluthiacet-methyl, sulcotrione, norflurazon, clomazone, bilanafos, asulam, flufenacet, dimethenamid-P, sulfentrazone, thiobencarb, 2,4-D and clopyralid, as well as their analogues such as salts, acids, esters and amides.

The herbicidal composition of the present invention is generally as follows, although it depends also on the relative activities of the respective Components.

Per 1 part by weight of Component A, Component B is from 0.001 to 100 parts by weight, preferably from 0.01 to 50 parts by weight, more preferably from 0.05 to 30 parts by weight, and when Component D is incorporated, D is from 0.01 to 100 parts by weight, preferably from 0.05 to 30 parts by weight.

Further, per 1 part by weight of Component A, Component B is from 0.001 to 100 parts by weight, preferably from 0.01 to 50 parts by weight, more preferably from 0.05 to 30 parts by weight, Component C is from 0.001 to 100 parts by weight, preferably from 0.01 to 50 parts by weight, more preferably from 0.05 to 30 parts by weight, and when Component D is incorporated, Component D is from 0.001 to 100 parts by weight, preferably from 0.01 to 100 parts by weight, more preferably from 0.05 to 30 parts by weight.

The herbicidal composition of the present invention may contain additive components which are commonly used for agricultural formulations, as the case requires.

Such additive components may, for example, be a carrier such as a solid carrier or a liquid carrier, a surfactant, a binder or an adhesion-imparting agent, a thickener, a coloring agent, an extender, a spreader, an anti-freezing agent, an anti-caking agent, a disintegrating agent and a stabilizing agent.

Further, an antiseptic, plant segments, etc. may be used as additive components, as the case requires. Such additive components may be used alone or in combination as a mixture of two or more of them.

Such additive components will be described.

The solid carrier may, for example, be a natural mineral such as quartz, clay, kaolinite, pyrophillite, sericite, talc, bentonite, acid clay, attapulgite, zeolite or diatomaceous earth; an inorganic salt such as calcium carbonate, ammonium sulfate, sodium sulfate or potassium chloride; synthetic silicic acid or synthetic silicate; an organic solid carrier such as starch, cellulose or plant powder; or a plastic carrier such as polyethylene, polypropylene or polyvinylidene chloride. They may be used alone or in combination as a mixture of two or more of them.

The liquid carrier may, for example, be an alcohol which may be classified into a monohydric alcohol such as methanol, ethanol, propanol, isopropanol or butanol, and a polyhydric alcohol such as ethylene glycol, diethylene glycol, propylene glycol, hexylene glycol, polyethylene glycol, polypropylene glycol or glycerol; a polyhydric alcohol derivative such as propylene type glycol ether; a ketone such as acetone, methyl ethyl ketone, methyl isobutyl ketone, diisobutyl ketone or cyclohexanone; an ether such as ethyl ether, dioxane, cellosolve, dipropyl ether or tetrahydrofuran, an aliphatic hydrocarbon such as normal paraffin, naphthene, isoparaffin, kerosine or mineral oil; an aromatic hydrocarbon such as benzene, toluene, xylene, solvent naphtha or alkyl naphthalene, a halogenated hydrocarbon such as dichloroethane, chloroform or carbon tetrachloride; an ester such as ethyl acetate, diisopropyl phthalate, dibutyl phthalate, dioctyl phthalate or dimethyl adipate; a lactone such as γ-butyrolactone; an amide such as dimethylformamide, dimethylformamide, dimethylacetamide or N-alkylpyrrolidinone; a nitrile such as acetonitrile; a sulfur compound such as dimethylsulfoxide; a vegetable oil such as soybean oil, rapeseed oil, cotton oil or castor oil; or water. They may be used alone or in combination as a mixture of two or more of them.

The surfactant is not particularly limited, but it is preferably one to be gelled or swelled in water. It may, for example, be a non-ionic surfactant such as a sorbitan fatty acid ester, a polyoxyethylene sorbitan fatty acid eater, a sucrose fatty acid ester, a polyoxyethylene fatty acid ester, a polyoxyethylene resin acid ester, a polyoxyethylene fatty acid diester, a polyoxyethylene alkyl ether, a polyoxyethylene alkyl phenyl ether, a polyoxyethylene dialkyl phenyl ether, a polyoxyethylene alkyl phenyl ether formalin condensate, a polyoxyethylene polyoxypropylene block copolymer, an alkyl polyoxyethylene polypropylene block polymer ether, a polyoxyethylene alkylamine, a polyoxyethylene fatty acid amide, a polyoxyethylene fatty acid bisphenyl ether, a polyalkylene benzyl phenyl ether, a polyoxyalkylene styryl phenyl ether, an acetylenediol, a polyoxyalkylene-added acetylenediol, a polyoxyethylene ether type silicon, an ester type silicon, a fluorinated surfactant, a polyoxyethylene castor oil, a polyoxyethylene hardened castor oil; an anionic surfactant such as an alkyl sulfate, a polyoxyethylene alkyl ether sulfate, a polyoxyethylene alkyl phenyl ether sulfate, a polyoxyethylene styryl phenyl ether sulfate, an alkyl benzenesulfonate, a lignin sulfonate, an alkylsulfosuccinate, a naphthalenesulfonate, an alkylnaphthalenesulfonate, a salt of a formalin condensate or naphthalenesulfonate, a salt of a formalin condensate of an alkylnaphthalenesulfonate, a fatty acid salt, a polycarboxylic acid salt, an N-methyl-fatty acid sarcosinate, a resin acid salt, a polyoxyethylene alkyl ether phosphate or a polyoxyethylene alkyl phenyl ether phosphate; a cationic surfactant such as a laurylamine hydrochloride, a stearylamine hydrochloride, an oleylamine hydrochloride, a stearylamine acetate, a stearylaminopropylamine acetate, an alkyltrimethylammonium chloride, or an alkyldimethylbenzalkonium chloride; or an amphoteric surfactant such as an amino acid type or a betain type. These surfactants may be used alone or in combination as a mixture of two or more of them.

Further, the binder or adhesive-imparting agent may, for example, be carboxymethylcellulose or its salt, dextrin, water-soluble starch, guar gum, sucrose, polyvinylpyrrolidone, gum arabic, polyvinyl alcohol, polyvinyl acetate, polysodium acrylate, a polyethylene glycol having an average molecular weight of 6,000 to 20,000, a polyethylene oxide having an average molecular weight of 100,000 to 5,000,000 or a natural phosphatide (such as cephalinic acid or lecithin).

The thickener may, for example, be a water-soluble polymer such as xanthan gum, guar gum, carboxylmethylcellulose, polyvinylpyrrolidone, carboxyvinyl polymer, acrylic polymer, starch derivative or polysaccharide; or an inorganic fine powder such as high purity bentonite or white carbon.

The coloring agent may, for example, be an inorganic pigment such as iron oxide, titanium oxide or Prussian blue; or an organic dye such as an arizarin dye, an azo dye or a metal phthalocyanine dye.

The extender may, for example, be a silicon type surfactant, a cellulose powder, dextrin, processed starch, a polyaminocarboxylic acid chelate compound, crosslinked polyvinylpyrrolidone, maleic acid and a styrene, a methacrylic acid copolymer, a half ester of a polymer of a polyhydric alcohol with a dicarboxylic anhydride, or a water-soluble salt of a polystyrene sulfonic acid.

The spreader may, for example, be various surfactants such as sodium dialkylsulfosuccinate, a polyoxyethylene alkyl ether, a polyoxyethylene alkyl phenyl ether or a polyoxyethylene fatty acid ester, paraffin, terpene, a polyamide resin, a polyacrylate, a polyoxyethylene, wax, a polyvinyl alkyl ether, an alkylphenol formalin condensate, or a synthetic resin emulsion.

The anti-freezing agent may, for example, be a polyhydric alcohol such as ethylene glycol, diethylene glycol, propylene glycol or glycerol.

The anticaking agent may, for example, be starch, alginic acid, a polysaccharide such as mannose or galactose, polyvinylpyrrolidone, white carbon, ester gum or petroleum resin.

The disintegrating agent may, for example, be sodium tripolyphosphate, sodium hexamethaphosphate, stearic acid metal salt, a cellulose powder, dextrin, a methacrylate copolymer, a polyvinylpyrrolidone, a polyaminocarboxylic acid chelate compound, a styrene sulfonate/isobutylene/maleic anhydride copolymer or a starch/polyacrylonitrile graft copolymer.

The stabilizer may, for example, be a drying agent such as zeolite, quick lime or magnesium oxide; an anti-oxidation agent such as a phenol type, an amine type, a sulfur type or a phosphorus type; or an ultraviolet absorber such as a salicylic acid type or a benzophenone type.

The antiseptic may, for example, be potassium sorbate or 1,2-benzthiazolin-3-one.

The plant segments may, for example, be sawdust, coconut shellflower, corn cob or tobacco stem.

In a case where the above-mentioned additive components are to be incorporated to the herbicidal composition of the present invention, their contents may be selected by weight such that the carrier is usually from 5 to 95%, preferably from 20 to 90%, the surfactant is usually from 0.1 to 30%, preferably from 0.5 to 10%, and other additives are usually from 0.1 to 30%, preferably from 0.5 to 10%.

The herbicidal composition of the present invention is used as formulated into an optional formulation such as a liquid formulation, an emulsifiable concentrate, a wettable powder, a dust, an oil formulation, a granular wettable powder, a flowable, an emulsified suspension agent, a granular formulation, a jumbo formulation or a suspoemulsion. At the time of such formulation, at least one other agricultural chemical such as another herbicide, a herbicidal microorganism (such as *Drechslera monoceras, Xanthomonas campestris* pv. *poae*), an insecticide, a fungicide, a plant-growth-controlling agent or a fertilizer may be mixed to obtain a mixed composition.

Fungicidal compounds which may be mixed or used in combination in the present invention, will be shown below.

Azaconazole, acibenzolar-S-methyl, azoxystrobin, amisulbrom, isoprothiolane, ipconazole, iprodione, iprovalicarb, imazalil, iprobenfos, iminoctadine-triacetate, imibenconazole, etridiazole, edifenphos, ethaboxam, epoxiconazole, oxadixyl, oxytetracycline, oxycarboxin, oxpoconazole fumarate, octhilinone, oxolinic acid, ofurace, orysastrobin, kasugamycin, captafol, carpropamid, carbendazime, carboxin, chinomethionat, captan, quintozene, guazatine, kresoxim-methyl, chlozolinate, chloroneb, chlorothalonil, chloroneb, cyazofamid, diethofencarb, diclocymet, dichlofluanid, diclomezine, dithianon, diniconazole, zineb, difenoconazole, difenzoquat, cyflufenamid, diflumetorim, cyproconazole, cyprodinil, simeconazole, dimethomorph, cymoxanil, dimoxystrobin, ziram, silthiofam, streptomycin, spiroxamine, zoxamide, dazomet, thiabendazole, thiram, thiophanate-methyl, thifluzamide, tecnazene, tecloftalam, tetraconazole, tebuconazole, dodine, dodemorph, triadimenol, triadimefon, triazoxide, tricyclazole, triticonazole, tridemorph, triflumizole, trifloxystrobin, triforine, tolylfluanid, tolclofos-methyl, nabam, nuarimol, paclobutrazol, validamycin, picoxystrobin, bitertanol, piperalin, hymexazol, pyraclostrobin, pyrazophos, pyrifenox, pyributicarb, pyribencarb, pyrimethanil, pyroquilon, vinclozolin, ferbam, famoxadone, phenazine oxide, fenamidone, fenarimol, fenoxanil, ferimzone, fenpiclonil, fenbuconazole, fenfuram, fenpropidin, fenpropimorph, fenhexamid, folpet, phthalide, bupirimate, fuberidazole, blasticidin-S, furametpyr, furalaxyl, fluazinam, fluoxastrobin, fluopicolide, fluoroimide, fluquinconazole, fludioxonil, flusilazole, flusulfamide, flutolanil, flutriafol, flumorph, proquinazid, prochloraz, procymidone, prothioconazole, propamocarb, propiconazole, propineb, probenazole, bromuconazole, hexaconazole, benalaxyl, benomyl, pefurazoate, penconazole, pencycuron, benthiavalicarb-isopropyl, boscalid, fosetyl, polyoxins, polycarbamate, folpet, mandipropamid, mancozeb, maneb, myclobutanil, milneb, methasulfocarb, metalaxyl, metalaxyl-M, metiram, metconazole, metominostrobin, metrafenone, mepanipyrim, mepronil, TF-991, penthiopyrad, a silver compound, an inorganic copper compound, an organic copper compound, a sulfur compound, an organic zinc compound, potassium hydrogencarbonate, sodium hydrogencarbonate, fatty acid glyceride, extract from mushroom, *Erwinia, pseudomonas, Bacillus, Talaromyces, Trichoderma, Fusarium.*

Further, insecticidal compounds which may be mixed or used in combination in the present invention will be shown below.

1,3-dichloropropene, acrinathrin, azamethiphos, azinphos-ethyl, azinphos-methyl, acequinocyl, acetamiprid, acetoprole, acephate, azocyclotin, abamectin, amitraz, alanycarb, aldicarb, alpha-cypermethrin, allethrin, isocarbophos, isoxathion, isoprocarb, imicyafos, imidacloprid, imiprothrin, indoxacarb, esfenvalerate, ethiofencarb, ethion, ethiprole, etoxazole, etofenprox, ethoprophos, emamectin, endosulfan, empenthrin, oxamyl, oxydemeton-methyl, omethoate, sodium olate, cadusafos, cartap, carbaryl, carbosulfan, carbofuran, gamma-cyhalothrin, xylylcarb, quinalphos, kinoprene, quinomethionate, coumaphos, clothianidin, clofentezine, chromafenozide, chlorethoxyfos, chlordane, chlorpyrifos, chlorpyrifos-methyl, chlorfenapyr, chlorfenvinphos, chlorfluazuron, chlormephos, cyanophos, diafenthiuron, dienochlor, dicrotophos, dichlofenthion, cycloprothrin, dichlorvos, disulfoton, dinotefuran, cyhalothrin, cyphenothrin, cyfluthrin, diflubenzuron, cyhexatin, cyflumetofen, cypermethrin, dimethylvinphos, dimethoate, silafluofen, cyromazine, spinosad, spirodiclofen, spirotetramat, supiromesifen, sulprofos, sulfotep, zeta-cypermethrin, diazinon, tau-fluvalinate, thiacloprid, thiamethoxam, thiodicarb, thiocyclam, thiosultap-sodium, thiofanox, thiometon, tetrachlorvinphos, tetradifon, tetramethrin, tebupirimfos, tebufenozide, tebufenpyrad, tefluthrin, teflubenzuron, temephos, deltamethrin, terbufos, tralomethrin, transfluthrin, triazamate, triazophos, trichlorfon, triflumuron, trimethacarb, tolfenpyrad, naled, nitenpyram, nemadectin, novaluron, noviflumuron, hydroprene, vamidothion, parathion, parathion-methyl, halfenprox, halofenozide, bioallethrin, bioresmethrin, bistrifluron, pyridaphenthion, bifenazate, bifenthrin, pymetrozine, pyraclofos, pyridafenthion, pyridaben, pyridalyl, pyriproxyfen, pirimicarb, pyrimidifen, pirimiphos-methyl, pyrethrins, fentrifanil, fipronil, fenazaquin, fenamiphos, fenitrothion, fenoxycarb, fenothiocarb, phenothrin, fenobucarb, fenthion, phenthoate, fenvalerate, fenpyroximate, fenbutatinoxide, fenpropathrin, butocarboxim, butoxycarboxim, buprofezin, furathiocarb, prallethrin, fluacrypyrim, flucycloxuron, flucythrinate, flusulfamide, fluvalinate, flupyrazofos, flufenoxuron, flubendiamide, flumethrin, flufenerim, prothiofos, flonicamid, propaphos, propargite, propoxur, profenofos, propetamphos, bromopropylate, beta-cypermethrin, beta-cyfluthrin, hexaflumuron, hexythiazox, heptenophos, permethrin, bensultap, bendiocarb, benfuracarb, phoxim, phosalone, fosthiazate, phosphamidon, phosmet, formetanate, phorate, machin oils, malathion, milbemectin, mecarbam, mesulfenfos, methomyl, metaldehyde, metaflumizone, metham-sodium, metham-ammonium, methamidophos, methiocarb, methidathion, methyl isothiacyanate, methoxyfenozide, methothrin, methoprene, metolcarb, mevinphos, monocrotophos, lambda-cyhalothrin, rynaxypyr, lufenuron, resmethrin, lepimectin, rotenone, CL900167, cryolite, DCIP, EPN, MEP, pyrifluquinazon, RU15525, spinetoram, XME, ZXI8901.

At the time of using the mixed herbicidal composition of the present invention, the active ingredients may be used directly, or a composition containing the desired active ingredients may be formulated, or the respective active ingredients may separately be formulated and then mixed. In application, the respective active ingredients of the composition of the present invention may be separately applied or simultaneously applied. Further, the composition of the present invention may be used as diluted with a liquid such as water or a fertilizer, or as deposited on a carrier such as a solid fertilizer, sand or soil, or on seeds or tubers of plants. With respect to the application sites, the composition of the present invention may be applied to a place where weeds will be germinated or to the plants themselves.

The herbicidal composition of the present invention exhibits excellent herbicidal effects at a low dose over a wide range from pre-emergence to post-emergence of various weeds problematic in e.g. upland fields, non-tilled crop fields or non-agricultural fields such as roads, parks, slopes, gardens or forests, including, for example, gramineous weeds such as barnyardgrass (*Echinochloa crus-galli*), crabgrass (*Digitaria ciliaris*), greenfoxtail (*Setaria viridis*), annual bluegrass (*Poa annua*), johnsongrass (*Sorghum halepense*), blackgrass (*Alopecurus myosuroides*), wild oat (*Avena fatua*), broadleaf weeds such as pale smartweed (*Polygonum lapathifolium*), slender amaranth (*Amaranthus viridis*), common lambsquater (*Chenopodium album*), common chickweed (*Stellaria media*), velvetleaf (*Abutilon theophrasti*), prickly sida (*Sida spinosa*), hempsesbania (*Sesbania exaltata*), common ragweed (*Ambrosia artemisifolia*), morningglory (*Ipomoea* spp), and perennial and annual cyperaceous weeds such as purple nutsedge (*Cyperus rotundus*), himekugu (*Cyperus brevifolius* var. *leiolepis*), annual sedge (*Cyperus microiria*) and rice flatsedge (*Cyperus iria*).

Particularly, it is capable of effectively controlling the main weeds in upland fields including dicotyledonous plants such as wild buckwheat (*Polygonum convolvulus*), pale smartweed (*Polygonum lapathifolium* L.), common purslane (*Portulaca oleracea*), common lambsquater (*Chenopodium album*), redroot pigweed (*Amaranthus retroflexus* L.), wild mustard (Kedlock) (*Brassica arvensis*), hempsesbania (*Sesbania exaltata*), sicklepod (*Cassia obtusifolia*), velvetleaf (*Abutilon theophrasti*), prickly sida (*Sida spinosa*), ivyleaf morningglory (*Ipomoea hederacea*), Jimsonweed (*Datura stramonium*), black nightshade (*Solanum nigrum*), common cocklebur (*Xanthium strumarium*), sunflower (*Helianthus annuus*), field bindweed (*Convolvulus arvensis*), *Euphorbia helioscopia* L. devils beggarticks (*Bidens frondosa*), common ragweed (*Ambrosia artemisifolia*), and monocotyledonous plants such as gramneae (*Echinochloa crus-galli* var. *crusgalli*), greenfoxtail (*Setaria viridis*), Foxtail grass (*Setaria faberi*), *Setaria glauca*, crabgrass (*Digitaria ciliaris*), goosegrass (*Eleusine indica*), johnsongrass (*Sorghum halepense*), quackgrass (*Agropyron repens*) and shattercane (*Sorghum vulgare*).

Further, it is capable of controlling annual weeds such as Rice barnyardgrass (*Echinochloa oryzicola*), umbrellaplant (*Cyperus difformis*), monochoria (*Monochorea vaginalis*) and false pimpernel (*Lindernia pyxidaria*), and perennial weeds such as water nutgrass (*Cyperus serotinus*), water chestnut (*Eleocharis kuroguwai*) and japanese bulrush (*Scirpus juncoides*), which germinate in paddy fields, over a wide range from pre-emergence to post-emergence.

The herbicidal composition of the present invention is highly safe to crop plants and may be used for crop plants or useful plants such as rice, wheat, barley, corn, grain sorghum, soybeans, cotton, sugar beet, rapeseed, sugarcane, lawn grass, tea, fruit trees, vegetables, flowers and trees. Here, the crop plants and useful plants include so-called genetically modified crop plants and plants showing resistance against herbicides, pests, diseases, etc., by breeding and selection, such as corn (such as PIOEER 31R87 RR), soybean (such as (ASGROW SN79624 RR), cotton (such as FIBERMAX 960BR), rapeseed, sugarcane, etc., which were transformed by genetic engineering and showing resistance against herbicides, pests, diseases, etc.

The composition of the present invention is preferably applied in the form of a formulation comprising components A and B or components A, B and C in a total amount of preferably from 0.5 to 90 wt %, more preferably from 1 to 80 wt %. The formulation of the composition of the present invention may be applied as it is, but an emulsifiable concentrate, a wettable powder, a suspension formulation or the like is usually applied as its prescribed amount is diluted with water in an amount of from 10 to 2,000 liter per 1 hectare.

Further, the dose of the composition of the present invention may vary depending upon the blend ratio, the weather conditions, the type of formulation, the application season, the application method, the application site, weeds to be controlled and crop plants. However, the composition is preferably applied in a total amount of components A and B or components A, B and C being from 1 g to 10,000 g, preferably from 5 g to 4,000 g, more preferably from 10 g to 1,000, per 1 ha (hectare).

EXAMPLES

Now, the present invention will be described in further detail with reference to Examples, but it should be understood that the present invention is by no means restricted to such specific Examples. In the following Examples, "parts" means "parts by weight".

Formulation Example 1

Wettable Powder

The following components are mixed, and the obtainable mixture is pulverized to obtain a wettable powder.

| | |
|---|---|
| Compound No. 3-0054 | 5 parts |
| Sulfentrazone | 5 parts |
| Polyoxyethyleneoctyl phenyl ether | 0.5 part |
| Sodium salt of alkylnaphthalenesulfonic acid formalin condensate | 0.5 part |
| Diatomaceous earth | 12 parts |
| Clay | 77 parts |

Formulation Example 2

Wettable Powder

The following components are mixed, and the obtainable mixture is pulverized to obtain a wettable powder.

| | |
|---|---|
| Compound No. 3-0054 | 5 parts |
| Sulcotrione | 10 parts |
| Atrazine | 25 parts |
| Polyoxyethyleneoctyl phenyl ether | 0.5 part |
| Sodium alkylnaphthalenesulfonic acid-formalin condensate | 0.5 part |
| Diatomaceous earth | 10 parts |
| Clay | 49 parts |

Formulation Example 3

Wettable Powder

The following components are mixed, and the obtainable mixture is pulverized to obtain a wettable powder.

| | |
|---|---|
| Compound No. 3-0054 | 5 parts |
| Atrazine | 30 parts |
| Benoxacor | 0.5 part |
| Polyoxyethyleneoctyl phenyl ether | 0.5 part |

-continued

| | |
|---|---|
| Sodium alkylnaphthalenesulfonic acid-formalin condensate | 0.5 part |
| Diatomaceous earth | 12 parts |
| Clay | 51.5 parts |

Formulation Example 4

Wettable Powder

The following components are mixed, and the obtainable mixture is pulverized to obtain a wettable powder.

| | |
|---|---|
| Compound No. 3-0054 | 5 parts |
| Sulcotrione | 10 parts |
| Atrazine | 25 parts |
| Benoxacor | 0.5 part |
| Polyoxyethyleneoctyl phenyl ether | 0.5 part |
| Sodium salt of alkylnaphthalenesulfonic acid-formalin condensate | 0.5 part |
| Diatomaceous earth | 10 parts |
| Clay | 48.5 parts |

Formulation Example 5

Granular Wettable Powder

The following components are kneaded and extrusion-granulated. The obtained granules are dried by a fluidized bed dryer to obtain a granular wettable powder.

| | |
|---|---|
| Compound No. 3-0054 | 10 parts |
| Chlorimuron | 2.5 parts |
| Sodium ligninsulfonate | 5 parts |
| Polyoxyetylene alkyl aryl ether | 1 part |
| Calcium carbonate | 81.5 parts |
| Water | 10 parts |

Formulation Example 6

Flowable Formulation

The following components are mixed by a high speed stirrer and pulverized by a wet pulverizer to obtain a flowable formulation.

| | |
|---|---|
| Compound No. 3-0054 | 5 parts |
| Sulcotrione | 10 parts |
| Atrazine | 25 parts |
| Benoxacor | 0.5 part |
| Sodium ligninsulfonate | 2 parts |
| Polyoxyethylene alkyl aryl ether ammonium sulfate | 4 parts |
| Polyoxyethylene alkyl aryl ether | 0.5 part |
| Xanthene gum | 0.1 part |
| Bentonite | 0.5 part |
| Ethylene glycol | 10 parts |
| Water | 42.4 parts |

Now, with reference to Test Examples, the effects of the herbicidal composition of the present invention will be described.

Test Example 1

Test 1 on Herbicidal Effects Against Weeds and Phytotoxicity by Upland Soil Treatment In a plastic pot of 14 cm in length×23 cm in width×8 cm in depth, upland soil was filled, and seeds of soybean (GLXMA), corn (ZEAMX), *Ipomoea lacunosa* L. (IPOLA) and velvetleaf (ABUTH) were sown and covered with soil. A wettable powder prepared in accordance with Formulation Example 1 was weighed so that the active ingredients became the prescribed amounts, diluted with water and uniformly applied to the soil surface by means of a small size spray at a rate of 500 liters per 1 hectare. Thereafter, cultivation was carried out in a greenhouse, and on the 28th day after the treatment, the herbicidal effects and phytotoxicity were examined in accordance with the standards as identified in Table 15. The results are shown in Table 16.

In the following Tables, 3-0054 represents Compound No. 3-0054.

TABLE 15

| Index No. | Herbicidal effects (growth-inhibition degree) and phytotoxicity |
|---|---|
| 10 | Herbicidal effect or phytotoxicity of 100% |
| 9 | Herbicidal effect or phytotoxicity of at least 90% and less than 100% |
| 8 | Herbicidal effect or phytotoxicity of at least 80% and less than 90% |
| 7 | Herbicidal effect or phytotoxicity of at least 70% and less than 80% |
| 6 | Herbicidal effect or phytotoxicity of at least 60% and less than 70% |
| 5 | Herbicidal effect or phytotoxicity of at least 50% and less than 60% |
| 4 | Herbicidal effect or phytotoxicity of at least 40% and less than 50% |
| 3 | Herbicidal effect or phytotoxicity of at least 30% and less than 40% |
| 2 | Herbicidal effect or phytotoxicity of at least 20% and less than 30% |
| 1 | Herbicidal effect or phytotoxicity of at least 10% and less than 20% |
| 0 | Herbicidal effect or phytotoxicity of at least 0% and less than 10% |

TABLE 16

| Herbicidal compounds | Dose gai/ha | GLXMA | ZEAMX | IPOLA | ABUTH |
|---|---|---|---|---|---|
| 3-0054 | 25 | 0 | 0 | 1 | 6 |
| Pyrithiobac-sodium | 25 | 4 | 10 | 3 | 8 |
| 3-0054 + pyrithiobac-sodium | 25 + 25 | 4 | 10 | 9 | 10 |
| 3-0054 | 100 | 1 | 1 | 3 | 8 |

TABLE 16-continued

| Herbicidal compounds | Dose gai/ha | GLXMA | ZEAMX | IPOLA | ABUTH |
|---|---|---|---|---|---|
| Imazethapyr | 50 | 0 | 4 | 4 | 4 |
| 3-0054 + imazethapyr | 100 + 50 | 1 | 5 | 8 | 10 |
| 3-0054 | 100 | 1 | 1 | 3 | 8 |
| Imazaquin | 50 | 0 | 6 | 5 | 3 |
| 3-0054 + imazaquin | 100 + 50 | 1 | 9 | 10 | 10 |
| 3-0054 | 100 | 1 | 1 | 3 | 8 |
| Diuron | 800 | 8 | 8 | 7 | 10 |
| 3-0054 + diuron | 100 + 800 | 9 | 9 | 9 | 10 |
| 3-0054 | 50 | 0 | 0 | 2 | 7 |
| Sulfentrazone | 50 | 1 | 0 | 6 | 10 |
| 3-0054 + sulfentrazone | 50 + 50 | 4 | 1 | 9 | 10 |
| 3-0054 | 50 | 0 | 0 | 2 | 7 |
| Norflurazon | 400 | 1 | 9 | 6 | 10 |
| 3-0054 + norflurazon | 50 + 400 | 1 | 10 | 10 | 10 |
| 3-0054 | 100 | 1 | 1 | 3 | 8 |
| Clomazone | 200 | 0 | 7 | 6 | 10 |
| 3-0054 + clomazone | 100 + 200 | 2 | 9 | 8 | 10 |
| 3-0054 | 50 | 0 | 0 | 2 | 7 |
| Flufenacet | 200 | 2 | 1 | 4 | 7 |
| 3-0054 + flufenacet | 50 + 200 | 2 | 1 | 8 | 9 |
| 3-0054 | 50 | 0 | 0 | 2 | 7 |
| Dimethenamid-P | 400 | 2 | 1 | 5 | 7 |
| 3-0054 + dimethenamid-P | 50 + 400 | 1 | 1 | 9 | 9 |
| 3-0054 | 100 | 1 | 1 | 3 | 8 |
| Thiobencarb | 1600 | 0 | 0 | 2 | 10 |
| 3-0054 + thiobencarb | 100 + 1600 | 0 | 1 | 8 | 10 |
| 3-0054 | 100 | 1 | 1 | 3 | 8 |
| Clopyralid | 200 | 10 | 0 | 6 | 10 |
| 3-0054 + clopyralid | 100 + 200 | 10 | 1 | 8 | 10 |

Test Example 2

Test 2 on Herbicidal Effects Against Weeds and Phytotoxicity by Upland Soil Treatment The test on herbicidal effects and phytotoxicity against wheat (TRZAW), common chickweed (STEME) and Persian speedwell (VERPE) was carried out in the same manner as the above Test Example 1. The results are shown in Table 17.

TABLE 17

| Herbicidal compounds | Dose gai/ha | TRZAW | STEME | VERPE |
|---|---|---|---|---|
| 3-0054 | 18.8 | 0 | 5 | 7 |
| Isoproturon | 375 | 0 | 6 | 5 |
| 3-0054 + isoproturon | 18.8 + 375 | 0 | 9 | 9 |
| 3-0054 | 18.8 | 0 | 5 | 7 |
| Picolinafen | 16 | 0 | 5 | 6 |
| 3-0054 + picolinafen | 18.8 + 16 | 0 | 9 | 9 |
| 3-0054 | 18.8 | 0 | 5 | 7 |
| Trifluralin | 250 | 0 | 10 | 7 |
| 3-0054 + trifluralin | 18.8 + 375 | 0 | 10 | 10 |

Test Example 3

Test 3 on Herbicidal Effects Against Weeds and Phytotoxicity by Upland Soil Treatment The test on herbicidal effects and phytotoxicity against corn (ZEAMX), barnyardgrass (ECHCG), common chickweed (STEME) and common lambsquater (CHEAL) was carried out in the same manner as the above Test Example 1. The results are shown in Table 18.

TABLE 18

| Herbicidal compounds | Dose gai/ha | ZEAMX | ECHCG | STEME | CHEAL |
|---|---|---|---|---|---|
| 3-0054 | 62.5 | 0 | 10 | 5 | 4 |
| Prosulfocarb | 1600 | 0 | 2 | 5 | 5 |
| 3-0054 + prosulfocarb | 62.5 + 1600 | 0 | 10 | 9 | 8 |

Test Example 4

Test 4 on Herbicidal Effects Against Weeds and Phytotoxicity by Upland Soil Treatment The test on herbicidal effects and phytotoxicity against wheat (TRZAW), italian ryegrass (LOLMU), common chickweed (STEME) and common lambsquater (CHEAL) was carried out in the same manner as the above Test Example 1. The results are shown in Table 19.

TABLE 19

| Herbicidal compounds | Dose gai/ha | TRZAW | LOLMU | STEME |
|---|---|---|---|---|
| 3-0054 | 50 | 0 | 8 | 4 |
| Triallate | 1000 | 0 | 2 | 2 |
| 3-0054 + triallate | 50 + 1000 | 0 | 10 | 6 |

Test Example 5

Test 5 on Herbicidal Effects Against Weeds and Phytotoxicity by Upland Soil Treatment A field was tilled and fertilized, and seeds of *Brachiaria plantaginea* (BRAPL) and *Sida rhombifolia* (SIDRH) were sown and covered with soil. A wettable powder prepared in accordance with Formulation Example 1 was weighed so that the active ingredients became the prescribed amounts, diluted with water and uniformly applied to the soil surface by means of a sprayer at a rate of 200 liters per 1 hectare. Then, on the 60th day after the treatment, the herbicidal effects and phytotoxicity were examined in accordance with the standards as identified in Table 15. The results are shown in Table 20.

TABLE 20

| Herbicidal compounds | Dose gai/ha | BRAPL | SIDRH |
|---|---|---|---|
| 3-0054 | 150 | 8 | 7 |
| Ametryn | 1500 | 7 | 6 |
| 3-0054 + ametryn | 150 + 1500 | 9 | 9 |

Test Example 6

Test on Herbicidal Effects Against Weeds and Phytotoxicity by Foliage Treatment in Upland Filed In a plastic pot of 11 cm in length×11 cm in width×11 cm in depth, the upland soil was filled, and seeds of corn (ZEAMX), soybean (GLXMA), greenfoxtail (SETVI), shattercane (SORVU), redroot pigweed (AMARE), *Ipomoea lacunosa* L. (IPOLA) and velvetleaf (ABUTH) were sown and covered with soil.

Then, cultivation was carried out in a greenhouse for 10 days. Then, a wettable powder prepared in accordance with Formulation Example 1 was weighed so that active ingredients would be the prescribed amounts, diluted with water and uniformly applied on the soil surface by means of a small size spray at a rate of 500 liter per 1 hectare. Thereafter, cultivation was carried out in a greenhouse, and on the 21st day after the treatment, the herbicidal effects and phytotoxicity were examined in accordance with the standards as identified in Table 15. The results are shown in Table 21.

TABLE 21

| Herbicidal compounds | Dose gai/ha | ZEAMX | GLXMA | SETVI | SORVU | AMARE | IPOLA | ABUTH |
|---|---|---|---|---|---|---|---|---|
| 3-0054 | 25 | 0 | 0 | 4 | 0 | 5 | 0 | 0 |
| Quizalofop-ethyl | 25 | 10 | 0 | 10 | 10 | 0 | 0 | 0 |
| 3-0054 + quizalofop-ethyl | 25 + 25 | 10 | 0 | 10 | 10 | 6 | 1 | 0 |
| 3-0054 | 100 | 0 | 0 | 8 | 6 | 10 | 1 | 4 |
| Sethoxydim | 100 | 9 | 0 | 10 | 9 | 0 | 0 | 0 |
| 3-0054 + sethoxydim | 100 + 100 | 9 | 1 | 10 | 9 | 10 | 4 | 4 |
| 3-0054 | 50 | 0 | 0 | 7 | 4 | 7 | 0 | 0 |
| Bispyribac-sodium | 12.5 | 0 | 9 | 7 | 2 | 10 | 7 | 5 |
| 3-0054 + bispyribac-sodium | 50 + 12.5 | 1 | 9 | 8 | 5 | 10 | 9 | 7 |
| 3-0054 | 50 | 0 | 0 | 7 | 4 | 7 | 0 | 0 |
| Pyrithiobac-sodium | 50 | 8 | 9 | 6 | 6 | 10 | 9 | 7 |
| 3-0054 + pyrithiobac-sodium | 50 + 12.5 | 8 | 9 | 8 | 6 | 10 | 10 | 9 |
| 3-0054 | 100 | 0 | 0 | 8 | 6 | 10 | 1 | 4 |
| Pyrimisulfan | 25 | 2 | 2 | 6 | 8 | 10 | 9 | 10 |
| 3-0054 + pyrimisulfan | 100 + 25 | 0 | 2 | 10 | 8 | 10 | 10 | 10 |
| 3-0054 | 25 | 0 | 0 | 4 | 0 | 5 | 0 | 0 |
| Chlorimuron-ethyl | 6.3 | 4 | 0 | 1 | 5 | 10 | 9 | 10 |
| 3-0054 + chlorimuron-ethyl | 25 + 6.3 | 1 | 0 | 8 | 7 | 10 | 9 | 10 |
| 3-0054 | 100 | 0 | 0 | 8 | 6 | 10 | 1 | 4 |
| Bentazone | 400 | 0 | 0 | 2 | 0 | 7 | 8 | 10 |
| 3-0054 + bentazone | 100 + 400 | 0 | 1 | 9 | 8 | 10 | 9 | 10 |
| 3-0054 | 100 | 0 | 0 | 8 | 6 | 10 | 1 | 4 |
| Paraquat | 500 | 6 | 10 | 6 | 6 | 10 | 6 | 9 |
| 3-0054 + paraquat | 100 + 500 | 5 | 8 | 9 | 9 | 10 | 8 | 10 |
| 3-0054 | 50 | 0 | 0 | 7 | 4 | 7 | 0 | 0 |
| Fluthiacet-methyl | 10 | 0 | 0 | 2 | 0 | 10 | 9 | 10 |
| 3-0054 + fluthiacet-methyl | 50 + 10 | 0 | 0 | 9 | 7 | 10 | 9 | 10 |
| 3-0054 | 50 | 0 | 0 | 7 | 4 | 7 | 0 | 0 |
| Sulcotrione | 25 | 0 | 6 | 3 | 3 | 8 | 5 | 9 |
| 3-0054 + sulcotrione | 50 + 25 | 0 | 7 | 9 | 8 | 10 | 8 | 10 |
| 3-0054 | 50 | 0 | 0 | 7 | 4 | 7 | 0 | 0 |
| Bilanafos | 1000 | 9 | 9 | 9 | 10 | 10 | 10 | 10 |
| 3-0054 + bilanafos | 50 + 1000 | 9 | 9 | 10 | 10 | 10 | 10 | 10 |
| 3-0054 | 50 | 0 | 0 | 7 | 4 | 7 | 0 | 0 |
| Asulam | 1000 | 8 | 9 | 9 | 10 | 10 | 10 | 10 |
| 3-0054 + asulam | 50 + 1000 | 8 | 9 | 10 | 10 | 10 | 10 | 10 |
| 3-0054 | 50 | 0 | 0 | 7 | 4 | 7 | 0 | 0 |
| 2,4-D | 200 | 0 | 9 | 2 | 1 | 10 | 10 | 10 |
| 3-0054 + 2,4-D | 50 + 200 | 0 | 9 | 9 | 5 | 10 | 10 | 10 |

Test Example 7

Test on Effects of Reducing Phytotoxicity Against Corn by Upland Soil Treatment In a plastic pot of 11 cm in length×11 cm in width×11 cm in depth, upland soil was filled, and seeds of corn (ZEAMX) were sown and covered with soil. A wettable powder prepared in accordance with Formulation Example 1 was weighed so that the active ingredients would be the prescribed amounts, diluted with water and uniformly applied to the soil surface by means of a small size spray at a rate of 500 liter per 1 hectare. Then, cultivation was carried out in a greenhouse, and on the 21st day after the treatment, the phytotoxicity against corn was examined in accordance with the standards as identified in Table 15. The results are shown in Table 22.

TABLE 22

| Herbicidal compounds | Dose gai/ha | ZEAMX |
|---|---|---|
| 3-0054 | 500 | 3 |
| Sulcotrione | 1000 | 1 |
| Atrazine | 2500 | 0 |
| Benoxacor | 50 | 0 |
| 3-0054 + sulcotrione + atrazine | 500 + 1000 + 2500 | 4 |
| 3-0054 + sulcotrione + atrazine + benoxacor | 500 + 1000 + 2500 + 50 | 1 |
| 3-0054 | 500 | 3 |
| Dimethenamid-P | 1500 | 3 |
| Benoxacor | 50 | 0 |
| 3-0054 + dimethenamid-P | 500 + 1500 | 5 |
| 3-0054 + dimethenamid-P + benoxacor | 500 + 1500 + 50 | 1 |

INDUSTRIAL APPLICABILITY

The herbicidal composition of the present invention is highly safe to crop plants and capable of controlling various weeds problematic in e.g. paddy fields, upland fields or non-agricultural fields over a wide range of from pre-emergency to post-emergence.

The entire disclosure of Japanese Patent Application No. 2006-344409 filed on Dec. 21, 2006 including specification, claims and summary is incorporated herein by reference in its entirety.

What is claimed is:

1. A herbicidal composition, comprising a component A and a component B as active ingredients, wherein:
   component A is 3-[(5-difluoromethoxy-1-methyl-3-trifluoromethylpyrazol-4-yl)methylsulfonyl]-4,5-dihydro-5,5-dimethylisoxazole and salts thereof; and
   component B is at least one compound selected from the group consisting of clodinafop-propargyl, diclofop-methyl, cycloxydim, tepraloxydim, tralkoxydim, amidosulfuron, iodosulfulon-methyl-sodium, mesosulfuron-methyl, sulfosulfuron, tribenuron-methyl, imazamethabenz-methyl, imazamox, imazapic, florasulam, flucarbazone-sodium, terbuthylazine, hexazinone, chlorotoluron, tebuthiuron, fomesafen, pyraflufen-ethyl, flurtamone, acetochlor, metazachlor, S-metolachlor, isoxaben, fluoroxypyr, quinclorac, diflufenzopyr, difenzoquat, propoxycarbazone-sodium, and pinoxaden.

2. The herbicidal composition of claim 1, wherein component B is at least one compound selected from the group consisting of acetochlor, clodinafop-propargyl, diclofop-methyl, cycloxydim, tepraloxydim, tralkoxydim, amidosulfuron, mesosulfuron-methyl, sulfosulfuron, tribenuron-methyl, imazamethabenz-methyl, imazamox, imazapic, florasulam, hexazinone, chlorotoluron, pyraflufen-ethyl, metazachlor, S-metolachlor, isoxaben, fluoroxypyr, qinclorac and pinoxaden.

3. The herbicidal composition of claim 1, further comprising a component C as an active ingredient, wherein component C is at least one compound selected from the group consisting of atrazine, simazine, cyanazine, isoxaflutole, mesotrione, flumetsulam, imazethapyr, imazapyr, dicamba, clopyralid, prosulfuron, halosulfuron-methyl, rimsulfuron, bentazon, carfentrazone-ethyl, metribuzin, thifensulfuron-methyl, nicosulfuron, primisulfuron, cloransulam-methyl, glufosinate, glyphosate, sulfosate, pendimethalin, linuron, prometryne, diflufenican, flumioxazin, metolachlor, and salts thereof.

4. The herbicidal composition of claim 1, further comprising a component D as an active ingredient, wherein component D is at least one compound selected from the group consisting of Cloquintocet-Mexyl, fenchlorazole, fenchlorazole-ethyl, mefenpyr, mefenpyr-diethyl, isoxadifen, isoxadifen-ethyl, furilazole, benoxacor, dichlormid, MON4660, oxabetrinil, cyometrinil, fenclorim, cyprosulfamide, naphthalic anhydride, Flurazole, and salts thereof.

5. The herbicidal composition of claim 3, further comprising a component D as an active ingredient, wherein component D is at least one compound selected from the group consisting of Cloquintocet-Mexyl, fenchlorazole, fenchlorazole-ethyl, mefenpyr, mefenpyr-diethyl, isoxadifen, isoxadifen-ethyl, furilazole, benoxacor, dichlormid, MON4660, oxabetrinil, cyometrinil, fenclorim, cyprosulfamide, naphthalic anhydride, Flurazole, and salts thereof.

6. The herbicidal composition of claim 1, wherein the weight ratio of Component A:Component B is from 1:0.001 to 1:100.

7. The herbicidal composition according to claim 3, wherein the weight ratio of Component A:Component B:Component C is from 1:0.001:0.001 to 1:100:100.

8. The herbicidal composition according to claim 4, wherein the weight ratio of Component A:Component B:Component D is from 1:0.001:0.001 to 1:100:100.

9. The herbicidal composition according to claim 5, wherein the weight ratio of Component A:Component B:Component C:Component D is from 1:0.001:0.001:0.001 to 1:100:100:100.

10. A herbicidal composition, comprising the herbicidal composition of claim 1, in a sufficient amount to exhibit a herbicidal activity, and at least one inert liquid carrier, solid carrier, or both, and optionally at least one surfactant.

11. A method for preparing the herbicidal composition of claim 1, the method comprising mixing:
   component A;
   component B;
   at least one inert liquid carrier, solid carrier, or both; and
   a surfactant.

12. A method for controlling unwanted plants, comprising applying the herbicidal composition of claim 1, simultaneously or dividedly, before, during and/or after germination of the unwanted plants.

13. The herbicidal composition of claim 1, wherein component B is at least one compound selected from the group consisting of flucarbazone-sodium, iodosulfulon-methyl-sodium, tebuthiuron, terbuthylazine, fomesafen, flurtamone, diflufenzopyr, difenzoquat and propoxycarbazone-sodium.

* * * * *